United States Patent
Wang et al.

(10) Patent No.: US 11,713,300 B2
(45) Date of Patent: Aug. 1, 2023

(54) PLATELET AGGREGATION INHIBITOR, PREPARATION AND USES THEREOF

(71) Applicant: SHENYANG HINEWY PHARMACEUTICAL TECHNOLOGY CO., LTD., Liaoning (CN)

(72) Inventors: Shaojie Wang, Liaoning (CN); Yu Lei, Liaoning (CN); Bing Zhang, Liaoning (CN)

(73) Assignee: SHENYANG HINEWY PHARMACEUTICAL TECHNOLOGY CO., LTD., Shenyang (CN)

( * ) Notice: Subject to any disclaimer, the term of this patent is extended or adjusted under 35 U.S.C. 154(b) by 63 days.

(21) Appl. No.: 17/154,012

(22) Filed: Jan. 21, 2021

(65) Prior Publication Data
US 2022/0064127 A1    Mar. 3, 2022

(30) Foreign Application Priority Data
Aug. 31, 2020   (CN) ......................... 202010891683.X

(51) Int. Cl.
| | | |
|---|---|---|
| C07D 233/90 | (2006.01) | |
| C07D 401/04 | (2006.01) | |
| C07D 403/12 | (2006.01) | |
| C07D 413/10 | (2006.01) | |

(52) U.S. Cl.
CPC ......... *C07D 233/90* (2013.01); *C07D 401/04* (2013.01); *C07D 403/12* (2013.01); *C07D 413/10* (2013.01)

(58) Field of Classification Search
None
See application file for complete search history.

(56) References Cited

U.S. PATENT DOCUMENTS 10,435,403 B2    10/2019   Teller et al.

FOREIGN PATENT DOCUMENTS

| CN | 111440146 A | 7/2020 |
|---|---|---|
| WO | 2020127504 A1 | 6/2020 |

OTHER PUBLICATIONS

Database Registry Chemical Abstracts Service, Columbus, Ohio, Accession No. RN 1408336-39-9. Entered STN: Nov. 30, 2012.*

* cited by examiner

*Primary Examiner* — Samantha L Shterengarts

(57) ABSTRACT

This disclosure relates to medicines, and more particularly to a platelet aggregation inhibitor, a pharmaceutical composition containing the same and a preparation and application thereof. The platelet aggregation inhibitor provided herein is a compound of formula (I), or a pharmaceutically-acceptable salt, a tautomer or a pharmaceutically-acceptable solvate thereof. This application also provides an application of the compound of formula (I), or a pharmaceutically-acceptable salt, a tautomer, a pharmaceutically-acceptable solvate or a pharmaceutical composition thereof in the treatment of thrombus.

5 Claims, 1 Drawing Sheet

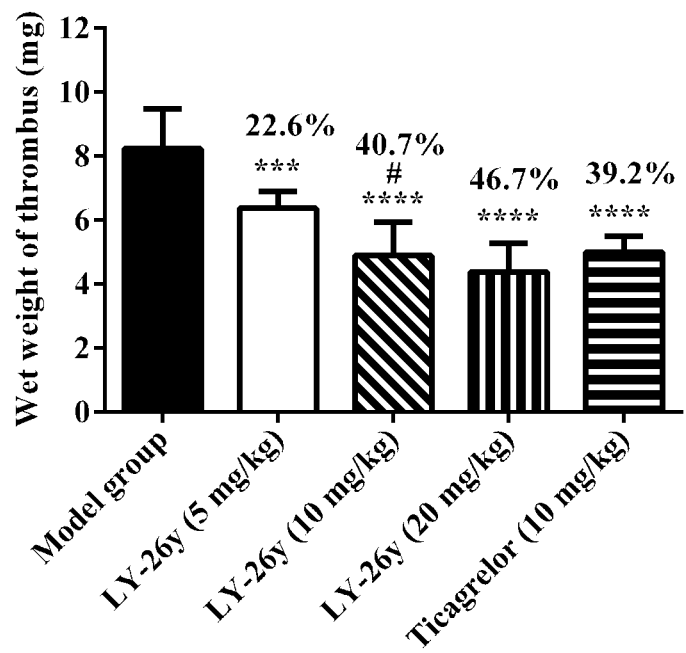

PLATELET AGGREGATION INHIBITOR, PREPARATION AND USES THEREOF

CROSS-REFERENCE TO RELATED APPLICATIONS

This application claims the benefit of priority from Chinese Patent Application No. 202010891683.X, filed on Aug. 31, 2020. The content of the aforementioned application, including any intervening amendments thereto, is incorporated herein by reference in its entirety.

TECHNICAL FIELD

This application relates to medicines, and more particularly to a platelet aggregation inhibitor, and a preparation and uses thereof.

BACKGROUND

Thromboembolic diseases, such as acute myocardial infarction and stroke, have the highest morbidity and mortality in developing countries. Pathologically, the thromboembolic diseases refer to the tissue and organ injuries caused by thrombosis or embolism formed in arteries and veins under the induction of various internal and external factors. Essentially, they pertain to cardiovascular and cerebrovascular diseases, and have high occurrence in clinic. Moreover, the thromboembolic diseases are also the cause and complication of many other cardiovascular and cerebrovascular diseases, and more unfortunately, the thrombus often causes irreversible and serious consequences once it occurs.

The formation of a stable platelet thrombus generally includes three stages: platelet adhesion, platelet activation and platelet aggregation. Currently, numerous strategies have been applied to interfere with platelet adhesion, activation or aggregation to inhibit the formation of pathological thrombosis. Considering that the platelet activation plays a key role in the development of thrombotic complications, antiplatelet therapy is still an important tool for clinical prevention and treatment of thrombotic diseases.

At present, some anti-platelet aggregation drugs, such as clopidogrel and ticagrelor, have been commercially available, but they still need to be improved due to the limited type and the existence of side effects (such as bleeding). Therefore, it is promising to develop a platelet aggregation inhibitor with high efficacy and low side effects of bleeding.

SUMMARY

An object of this application is to provide a compound of formula (I) for inhibiting the platelet aggregation, which can be used to prepare drugs for preventing and treating thrombotic diseases.

Technical solutions of this application are described as follows.

In a first aspect, this application provides a compound of formula (I), or a pharmaceutically-acceptable salt, a tautomer or a pharmaceutically-acceptable solvate thereof:

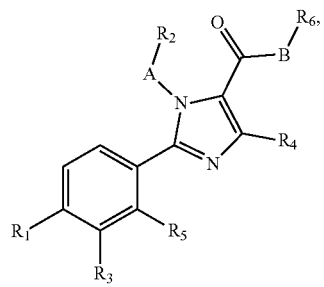

(I)

wherein $R_1$ is selected from the group consisting of hydrogen, hydroxyl, cyano, tetrazolyl, triazolyl, imidazolyl, nitro, halogen, $C_1$-$C_8$ linear and branched alkyl, $C_3$-$C_8$ cycloalkyl, $C_1$-$C_8$ linear and branched alkyloxy, $C_3$-$C_8$ cycloalkyloxy, $C_1$-$C_8$ linear and branched aliphatic alkylamino, $C_3$-$C_8$ aliphatic cycloalkylamino, $C_2$-$C_8$ linear and branched alkenyl, $C_2$-$C_8$ linear and branched alkenyloxy, $C_2$-$C_8$ linear and branched alkenylamino, $C_2$-$C_8$ linear and branched alkynyl, $C_2$-$C_8$ linear and branched alkynyloxy, $C_2$-$C_8$ linear and branched alkynylamino, and substituted and unsubstituted $C_6$-$C_{10}$ aryl, wherein a substituent on the substituted $C_6$-$C_{10}$ aryl is selected from the group consisting of halogen, hydroxyl, cyano, nitro, $C_1$-$C_6$ alkyl, $C_1$-$C_6$ alkyloxy, $C_1$-$C_6$ alkylamino, $C_1$-$C_6$ alkylcarbonyl, $C_1$-$C_6$ alkyloxycarbonyl and $C_1$-$C_6$ alkylaminocarbonyl;

$R_2$ is selected from the group consisting of hydrogen, hydroxyl, $C_1$-$C_8$ linear and branched alkyl, $C_3$-$C_8$ cycloalkyl, $C_2$-$C_8$ linear and branched alkenyl, $C_2$-$C_8$ linear and branched alkynyl, —$(CH_2)_n$—COOH, —$(CH_2)_n$—OH, —$(CH_2)_n$—CONH$_2$, —$(CH_2)_n$—NHOC$(CH_2)_m$CH$_3$, —$(CH_2)_n$—COOC$(CH_2)_m$CH$_3$ and substituted and unsubstituted $C_6$-$C_{10}$ aryl, wherein a substituent on the substituted $C_6$-$C_{10}$ aryl is selected from the group consisting of halogen, hydroxyl, cyano, nitro, $C_1$-$C_6$ alkyl, $C_1$-$C_6$ alkyloxy, $C_1$-$C_6$ alkylamino, —$(CH_2)_n$—COOH, —$(CH_2)_n$—OH, —$(CH_2)_n$—CONH$_2$, —$(CH_2)_n$—NHOC$(CH_2)_m$CH$_3$ and —$(CH_2)_n$—COOC$(CH_2)_m$CH$_3$; and n is selected from 1-6, and m is selected from 1-3;

A is selected from the group consisting of nitrogen atom, oxygen atom, hydrogen atom, carbon atom and sulfur atom;

$R_3$ is selected from the group consisting of hydrogen, cyano, tetrazolyl, triazolyl, imidazolyl, 1,2,4-oxadiazolyl, nitro, halogen, $C_1$-$C_6$ alkyl, $C_1$-$C_6$ alkylamino and $C_1$-$C_6$ alkoxy;

$R_4$ is selected from the group consisting of $C_1$-$C_6$ alkyl and substituted and unsubstituted $C_6$-$C_{10}$ aryl, wherein a substituent on the substituted aryl is selected from the group consisting of halogen, $C_1$-$C_6$ alkylamino, $C_1$-$C_6$ alkyl, $C_1$-$C_6$ alkoxy, nitro, hydroxyl, cyano and amino;

$R_5$ is selected from the group consisting of hydrogen, cyano, tetrazolyl, triazolyl, imidazolyl, 1,2,4-oxadiazolyl, nitro, fluorine, chlorine, bromine, $C_1$-$C_6$ alkyl, $C_1$-$C_6$ alkylamino and $C_1$-$C_6$ alkoxy;

$R_6$ is selected from the group consisting of hydrogen, $C_1$-$C_6$ alkyl, $C_1$-$C_6$ alkylamino, $C_1$-$C_6$ alkoxy and substituted and unsubstituted $C_6$-$C_{10}$ aryl, wherein a substituent on the substituted aryl is selected from the group consisting of halogen, $C_1$-$C_6$ alkylamino, $C_1$-$C_6$ alkoxy, $C_1$-$C_6$ alkyl, nitro, hydroxyl, cyano and amino; and B is selected from the group consisting of oxygen atom, nitrogen atom, carbon atom, sulfur atom and NH.

In some embodiments, in the formula (I), $R_1$ is selected from the group consisting of hydrogen, hydroxyl, cyano, tetrazolyl, triazolyl, imidazolyl, nitro, halogen, $C_1$-$C_8$ linear and branched alkyl, $C_1$-$C_8$ linear and branched alkyloxy, $C_1$-$C_8$ linear and branched aliphatic alkylamino, $C_2$-$C_8$ linear alkenyl, $C_2$-$C_8$ linear alkenyloxy, $C_2$-$C_8$ linear alkenylamino, $C_2$-$C_8$ linear alkynyl, $C_2$-$C_8$ linear alkynyloxy, $C_2$-$C_8$ linear alkynylamino and substituted and unsubstituted $C_6$-$C_{10}$ aryl, wherein a substituent on the substituted $C_6$-$C_{10}$ aryl is selected from the group consisting of halogen, hydroxyl, cyano, nitro, $C_1$-$C_6$ alkyl, $C_1$-$C_6$ alkyloxy, $C_1$-$C_6$ alkylamino, $C_1$-$C_6$ alkylcarbonyl, $C_1$-$C_6$ alkyloxycarbonyl, and $C_1$-$C_6$ alkylaminocarbonyl;

$R_2$ is selected from the group consisting of hydrogen, hydroxyl, $C_1$-$C_8$ linear alkyl, $C_2$-$C_8$ linear alkenyl, $C_2$-$C_8$ linear alkynyl, —$(CH_2)_n$—COOH, —$(CH_2)_n$—OH, —$(CH_2)_n$—CONH$_2$, —$(CH_2)_n$—NHOC$(CH_2)_m$CH$_3$, —$(CH_2)_n$—COOC$(CH_2)_m$CH$_3$ and substituted and unsubstituted $C_6$-$C_{10}$ aryl, wherein a substituent on the substituted $C_6$-$C_{10}$ aryl is selected from the group consisting of halogen, hydroxyl, cyano, nitro, $C_1$-$C_6$ alkyl, $C_1$-$C_6$ alkyloxy, $C_1$-$C_6$ alkylamino, —$(CH_2)_n$—COOH, —$(CH_2)_n$—OH, —$(CH_2)_n$—CONH$_2$, —$(CH_2)_n$—NHOC$(CH_2)_m$CH$_3$, and —$(CH_2)_n$—COOC$(CH_2)_m$CH$_3$; and n is selected from 1-6, and m is selected from 1-3;

A is selected from the group consisting of oxygen atom, hydrogen atom, and carbon atom;

$R_3$ is selected from the group consisting of hydrogen, cyano, tetrazolyl, triazolyl, imidazolyl, 1,2,4-oxadiazolyl, nitro, halogen, $C_1$-$C_6$ alkyl, $C_1$-$C_6$ alkylamino, and $C_1$-$C_6$ alkoxy;

$R_4$ is selected from the group consisting of $C_1$-$C_6$ alkyl and substituted and unsubstituted $C_6$-$C_{10}$ aryl, wherein a substituent on the substituted aryl is selected from the group consisting of halogen, $C_1$-$C_6$ alkylamino, $C_1$-$C_6$ alkyl, $C_1$-$C_6$ alkoxy, nitro, hydroxyl, cyano, and amino;

$R_5$ is selected from the group consisting of hydrogen, cyano, tetrazolyl, triazolyl, imidazolyl, 1,2,4-oxadiazolyl, nitro, fluorine, chlorine, bromine, $C_1$-$C_6$ alkyl, $C_1$-$C_6$ alkylamino and $C_1$-$C_6$ alkoxy;

$R_6$ is selected from the group consisting of hydrogen, $C_1$-$C_6$ alkyl, $C_1$-$C_6$ alkylamino, $C_1$-$C_6$ alkoxy and substituted and unsubstituted $C_6$-$C_{10}$ aryl, wherein a substituent on the substituted aryl is selected from the group consisting of halogen, $C_1$-$C_6$ alkylamino, $C_1$-$C_6$ alkoxy, $C_1$-$C_6$ alkyl, nitro, hydroxyl, cyano, and amino; and B is selected from the group consisting of oxygen atom, nitrogen atom and NH.

In some embodiments, in the formula (I), $R_1$ is selected from the group consisting of hydrogen, hydroxyl, cyano, tetrazolyl, triazolyl, imidazolyl, nitro, halogen, $C_1$-$C_6$ linear and branched alkyl, $C_1$-$C_6$ linear and branched alkyloxy, $C_1$-$C_6$ linear and branched aliphatic alkylamino, $C_2$-$C_6$ linear and branched alkenyl, $C_2$-$C_6$ linear and branched alkenyloxy, $C_2$-$C_6$ linear and branched alkenylamino, $C_2$-$C_6$ linear and branched alkynyl, $C_2$-$C_8$ linear and branched alkynyloxy, $C_2$-$C_8$ linear and branched alkynylamino and substituted and unsubstituted phenyl or benzyl, wherein a substituent on the substituted phenyl or benzyl is selected from the group consisting of halogen, hydroxyl, cyano, nitro, $C_1$-$C_6$ alkyl, $C_1$-$C_6$ alkyloxy, $C_1$-$C_6$ alkylamino, $C_1$-$C_6$ alkylcarbonyl, $C_1$-$C_6$ alkyloxycarbonyl and $C_1$-$C_6$ alkylaminocarbonyl;

$R_2$ is selected from the group consisting of hydrogen, hydroxyl, $C_1$-$C_6$ linear and branched alkyl, $C_2$-$C_6$ linear and branched alkenyl, $C_2$-$C_6$ linear and branched alkynyl, —$(CH_2)_n$—COOH, —$(CH_2)_n$—OH, —$(CH_2)_n$—CONH$_2$, —$(CH_2)_n$—NHOC$(CH_2)_m$CH$_3$, —$(CH_2)_n$—COOC$(CH_2)_m$CH$_3$ and substituted and unsubstituted

or phenyl or benzyl, wherein a substituent on the substituted

or phenyl or benzyl is selected from the group consisting of halogen, hydroxyl, cyano, nitro, $C_1$-$C_6$ alkyl, $C_1$-$C_6$ alkyloxy, $C_1$-$C_6$ alkylamino, —$(CH_2)_n$—COOH, —$(CH_2)_n$—OH, —$(CH_2)_n$—CONH$_2$, —$(CH_2)_n$—NHOC$(CH_2)_m$CH$_3$ and —$(CH_2)_n$—COOC$(CH_2)_m$CH$_3$; and n is selected from 1-6, and m is selected from 1-3;

A is selected from the group consisting of oxygen atom, hydrogen atom, and carbon atom;

$R_3$ is selected from the group consisting of hydrogen, cyano, tetrazolyl, triazolyl, imidazolyl, 1,2,4-oxadiazolyl, nitro, halogen, $C_1$-$C_6$ alkyl, $C_1$-$C_6$ alkylamino and $C_1$-$C_6$ alkoxy;

$R_4$ is selected from the group consisting of $C_1$-$C_6$ alkyl and substituted and unsubstituted phenyl, wherein a substituent on the substituted phenyl is selected from the group consisting of halogen, $C_1$-$C_6$ alkylamino, $C_1$-$C_6$ alkyl, $C_1$-$C_6$ alkoxy, nitro, hydroxyl, cyano, and amino;

$R_5$ is selected from the group consisting of hydrogen, cyano, tetrazolyl, triazolyl, imidazolyl, 1,2,4-oxadiazolyl, nitro, fluorine, chlorine, bromine, $C_1$-$C_6$ alkyl, $C_1$-$C_6$ alkylamino and $C_1$-$C_6$ alkoxy;

$R_6$ is selected from the group consisting of hydrogen, $C_1$-$C_6$ alkyl, $C_1$-$C_6$ alkylamino, $C_1$-$C_6$ alkoxy and substituted and unsubstituted $C_6$-$C_{10}$ aryl, wherein a substituent on the substituted aryl is selected from the group consisting of halogen, $C_1$-$C_6$ alkylamino, $C_1$-$C_6$ alkoxy, $C_1$-$C_6$ alkyl, nitro, hydroxyl, cyano and amino; and B is selected from the group consisting of oxygen atom, nitrogen atom and NH.

In some embodiments, in the formula (I), $R_1$ is selected from the group consisting of hydrogen, hydroxyl, cyano, tetrazolyl, triazolyl, imidazolyl, nitro, halogen atom, $C_1$-$C_6$ linear and branched alkyl and $C_1$-$C_6$ linear and branched alkyloxy;

$R_2$ is selected from the group consisting of hydrogen, hydroxyl, $C_1$-$C_6$ linear and branched alkyl, $C_2$-$C_6$ linear and branched alkenyl, $C_2$-$C_6$ linear and branched alkynyl, —$(CH_2)_n$—COOH, —$(CH_2)_n$—OH, —$(CH_2)_n$—CONH$_2$, —$(CH_2)_n$—NHOC$(CH_2)_m$CH$_3$, —$(CH_2)_n$—COOC$(CH_2)_m$CH$_3$ and substituted and unsubstituted

or phenyl or benzyl, wherein a substituent on the substituted

or phenyl or benzyl is selected from the group consisting of halogen, hydroxyl, cyano, nitro, $C_1$-$C_6$ alkyl, $C_1$-$C_6$ alkyloxy, $C_1$-$C_6$ alkylamino, —$(CH_2)_n$—COOH, —$(CH_2)_n$—OH, —$(CH_2)_n$—$CONH_2$, —$(CH_2)_n$—$NHOC(CH_2)_mCH_3$ and —$(CH_2)_n$—$COOC(CH_2)_mCH_3$; and n is selected from 1-6, and m is selected from 1-3;

A is selected from the group consisting of oxygen atom, hydrogen atom, and carbon atom;

$R_3$ is selected from the group consisting of hydrogen, cyano, tetrazolyl, triazolyl, imidazolyl, 1,2,4-oxadiazolyl, nitro, halogen, $C_1$-$C_6$ alkyl, $C_1$-$C_6$ alkylamino, and $C_1$-$C_6$ alkoxy;

$R_4$ is selected from the group consisting of $C_1$-$C_6$ alkyl and substituted and unsubstituted phenyl, wherein a substituent on the substituted phenyl is selected from the group consisting of halogen, $C_1$-$C_6$ alkylamino, $C_1$-$C_6$ alkyl, $C_1$-$C_6$ alkoxy, nitro, hydroxyl, cyano and amino;

$R_5$ is selected from the group consisting of hydrogen, cyano, tetrazolyl, triazolyl, imidazolyl, 1,2,4-oxadiazolyl, nitro, fluorine, chlorine, bromine, $C_1$-$C_6$ alkyl, $C_1$-$C_6$ alkylamino and $C_1$-$C_6$ alkoxy;

$R_6$ is selected from the group consisting of hydrogen, $C_1$-$C_6$ alkyl, $C_1$-$C_6$ alkylamino, $C_1$-$C_6$ alkoxy and substituted and unsubstituted phenyl, wherein a substituent on the substituted phenyl is selected from the group consisting of halogen, $C_1$-$C_6$ alkylamino, $C_1$-$C_6$ alkoxy, $C_1$-$C_6$ alkyl, nitro, hydroxyl, cyano and amino; and B is selected from the group consisting of oxygen atom, nitrogen atom and NH.

In some embodiments, in the formula (I), $R_1$ is selected from the group consisting of hydrogen, hydroxyl, cyano, tetrazolyl, triazolyl, imidazolyl, nitro, halogen atom, $C_1$-$C_6$ linear and branched alkyl and $C_1$-$C_6$ linear and branched alkyloxy;

$R_2$ is selected from the group consisting of hydrogen, hydroxyl, $C_1$-$C_6$ linear and branched alkyl, $C_2$-$C_6$ linear and branched alkenyl, $C_2$-$C_6$ linear and branched alkynyl, —$(CH_2)_n$—COOH, —$(CH_2)_n$—OH, —$(CH_2)_n$—$CONH_2$, —$(CH_2)_n$—$NHOC(CH_2)_mCH_3$, —$(CH_2)_n$—$COOC(CH_2)_mCH_3$ and substituted or unsubstituted

or phenyl or benzyl, wherein a substituent on the substituted

or phenyl or benzyl is selected from the group consisting of halogen, hydroxyl, cyano, nitro, $C_1$-$C_6$ alkyl, $C_1$-$C_6$ alkyloxy, $C_1$-$C_6$ alkylamino, —$(CH_2)_n$—COOH, —$(CH_2)_n$—OH, —$(CH_2)_n$—$CONH_2$, —$(CH_2)_n$—$NHOC(CH_2)_mCH_3$ and —$(CH_2)_n$—$COOC(CH_2)_mCH_3$; and n is selected from 1-6, and m is selected from 1-3;

A is selected from the group consisting of oxygen atom, hydrogen atom, and carbon atom;

$R_3$ is selected from the group consisting of hydrogen, cyano, tetrazolyl, triazolyl, imidazolyl and 1,2,4-oxadiazolyl;

$R_4$ is selected from the group consisting of $C_1$-$C_6$ alkyl and substituted and unsubstituted phenyl, wherein a substituent on the substituted phenyl is selected from the group consisting of halogen, $C_1$-$C_4$ alkyl and $C_1$-$C_4$ alkoxy;

$R_5$ is selected from the group consisting of hydrogen and cyano;

$R_6$ is selected from the group consisting of hydrogen, $C_1$-$C_4$ alkyl and substituted and unsubstituted phenyl, wherein a substituent on the substituted phenyl is selected from the group consisting of halogen atom, $C_1$-$C_6$ alkoxy and $C_1$-$C_6$ alkyl; and B is selected from the group consisting of oxygen atom, nitrogen atom and NH.

In some embodiments, the compound of formula (I) is selected from the group consisting of: ethyl 1-acetoxy-2-(3-cyano-4-isobutoxyphenyl)-4-methyl-1H-imidazole-5-carboxylate (LY-8a); ethyl 2-(3-cyano-4-hydroxyphenyl)-1-hydroxy-4-methyl-1H-imidazole-5-carboxylate (LY-8b); ethyl 2-(3-cyanophenyl)-1-hydroxy-4-methyl-1H-imidazole-5-carboxylate (LY-10); ethyl 2-[3-(1H-tetrazol-5-yl)phenyl]-1-hydroxy-4-methyl-1H-imidazole-5-carboxylate (LY-13); ethyl 1-hydroxy-4-methyl-2-[3-(5-oxo-4,5-dihydro-1,2,4-oxadiazol-3-yl)phenyl]-1H-imidazole-5-carboxylate (LY-15); ethyl 2-(3-cyanophenyl)-1-hydroxy-4-phenyl-1H-imidazole-5-carboxylate (LY-16); ethyl 2-(2-cyanophenyl)-1-hydroxy-4-methyl-1H-imidazole-5-carboxylate (LY-19); ethyl 2-(4-cyanophenyl)-1-methoxy-4-methyl-1H-imidazole-5-carboxylate (LY-22); ethyl 1-methoxy-2,4-dimethyl-2-phenyl-1H-imidazole-5-carboxylate (LY-25); ethyl 2-(3-cyanophenyl)-1-methoxy-4-methyl-1H-imidazole-5-carboxylate (LY-26a); ethyl 2-(3-cyanophenyl)-1-ethoxy-4-methyl-1H-imidazole-5-carboxylate (LY-26b); ethyl 2-(3-cyanophenyl)-1-isopropoxy-4-methyl-1H-imidazole-5-carboxylate (LY-26c); ethyl 1-(allyloxy)-2-(3-cyanophenyl)-4-methyl-1H-imidazole-5-carboxylate (LY-26d); ethyl 2-(3-cyanophenyl)-1-(2-ethoxyethoxy)-4-methyl-1H-imidazole-5-carboxylate (LY-26e); ethyl 2-(3-cyanophenyl)-1-(3-hydroxypropoxy)-4-methyl-1H-imidazole-5-carboxylate (LY-26f); ethyl 2-(3-cyanophenyl)-1-(2-ethoxy-2-oxoethoxy)-4-methyl-1H-imidazole-5-carboxylate (LY-26g); ethyl 1-(2-amino-2-oxoethoxy)-2-(3-cyanophenyl)-4-methyl-1H-imidazole-5-carboxylate (LY-26h); 2-{[2-(3-cyanophenyl)-5-(ethoxycarbonyl)-4-methyl-1H-imidazol-1-yl]oxy}acetic acid (LY-26i); ethyl 2-(3-cyanophenyl)-4-methyl-1-(pyridin-4-yl-methoxy)-1H-imidazole-5-carboxylate (LY-26j); ethyl 1-(benzyloxy)-2-(3-cyanophenyl)-4-methyl-1H-imidazole-5-carboxylate (LY-26k); ethyl 2-(3-cyanophenyl)-1-[(2-fluorobenzyl)oxy]-4-methyl-1H-imidazole-5-carboxylate (LY-26l); ethyl 2-(3-cyanophenyl)-1-[(3-fluorobenzyl)oxy]-4-methyl-1H-imidazole-5-carboxylate (LY-26m); ethyl 2-(3-cyanophenyl)-1-[(4-fluorobenzyl)oxy]-4-methyl-1H-imidazole-5-carboxylate (LY-26n); ethyl 1-[(2-chlorobenzyl)oxy]-2-(3-cyanophenyl)-4-methyl-1H-imidazole-5-carboxylate (LY-26o); ethyl 1-[(3-chlorobenzyl)oxy]-2-(3-cyanophenyl)-4-methyl-1H-imidazole-5-carboxylate (LY-26p); ethyl 1-[(4-chlorobenzyl)oxy]-2-(3-cyanophenyl)-4-methyl-1H-imidazole-5-carboxylate (LY-26q); ethyl 1-[(4-bromobenzyl)oxy]-2-(3-cyanophenyl)-4-methyl-1H-imidazole-5-carboxylate (LY-26r); ethyl 2-(3-cyanophenyl)-4-methyl-1-[(4-methylbenzyl)oxy]-1H-imidazole-5-carboxylate (LY-26s); ethyl 2-(3-cyanophenyl)-1-[(4-methoxybenzyl)oxy]-4-methyl-1H-imidazole-5-carboxylate (LY-26t); ethyl 2-(3-cyanophenyl)-1-{[4-(methoxycarbonyl)benzyl]oxy}-4-methyl-1H-imidazole-5-carboxylate (LY-26u); ethyl 2-(3-cyanophenyl)-4-methyl-1-[(4-nitrobenzyl)oxy]-1H-imidazole-5-carboxylate (LY-26v); ethyl 1-[(2-cyanobenzyl)oxy]-2-(3-cyanophenyl)-4-methyl-1H- imidazole-5-carboxylate (LY-26w); ethyl 1-[(3-cyanobenzyl)oxy]-2-(3-cyanophenyl)-4-methyl-1H-imidazole-5-carboxylate (LY-26x); ethyl 1-[(4-cyanobenzyl)oxy]-2-(3-cyanophenyl)-4-methyl-1H-imidazole-5-carboxylate (LY-26y); 2-(3-cyanophenyl)-1-hydroxy-4-methyl-1H-imidazole-5-carboxylic acid (LY-11); 2-(3-cyanophenyl)-1-methoxy-4-methyl-1H-imidazole-5-carboxylic acid (LY-27a); 2-(3-cyanophenyl)-1-ethoxy-4-methyl-1H-imidazole-5-carboxylic acid (LY-27b); 1-(allyloxy)-2-(3-cyanophenyl)-4-methyl-1H-imidazole-5-carboxylic acid (LY-27d); 1-(benzyloxy)-2-(3-cyanophenyl)-4-methyl-1H-imidazole-5-carboxylic acid (LY-27k); 2-(3-cyanophenyl)-4-methyl-1-[(4-methylbenzyl)oxy]-1H-imidazole-5-carboxylic acid (LY-27s); 1-[(4-cyanobenzyl)oxy]-2-(3-cyanophenyl)-4-methyl-1H-imidazole-5-carboxylic acid (LY-27y); 2-(3-cyanophenyl)-1-methoxy-4-methyl-N-propyl-1H-imidazole-5-carboxamide (LY-28a); 2-(3-cyanophenyl)-N-isopropyl-1-methoxy-4-methyl-1H-imidazole-5-carboxamide (LY-28b); 2-(3-cyanophenyl)-1-methoxy-4-methyl-N-phenyl-1H-imidazole-5-carboxamide (LY-28c); ethyl 2-(3-cyanophenyl)-1,4-dimethyl-1H-imidazole-5-carboxylate (LY-30a); and ethyl 2-(3-cyano-4-fluorophenyl)-1-hydroxy-4-methyl-1H-imidazole-5-carboxylate (LY-F1), as shown in the following formulas:

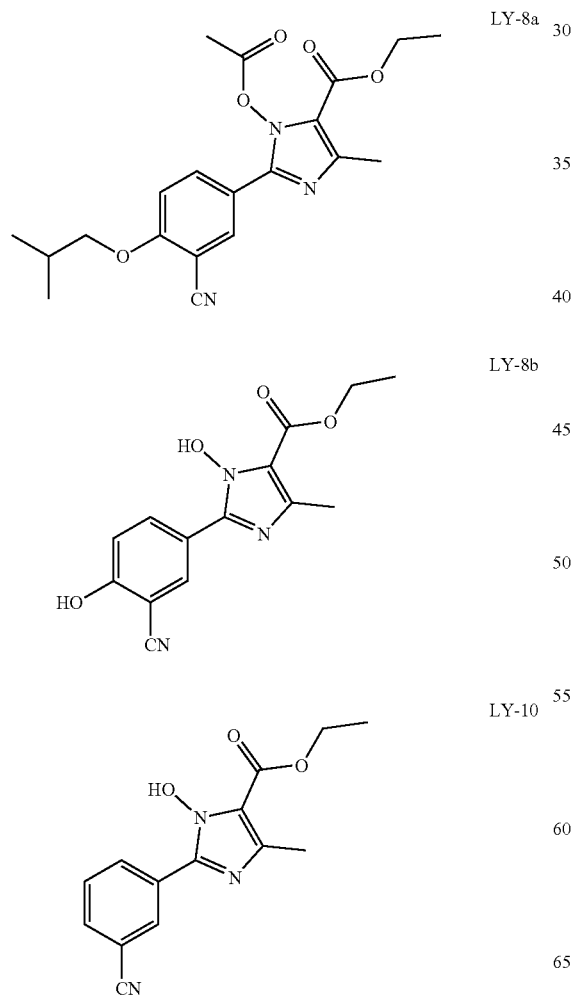

LY-8a

LY-8b

LY-10

LY-13

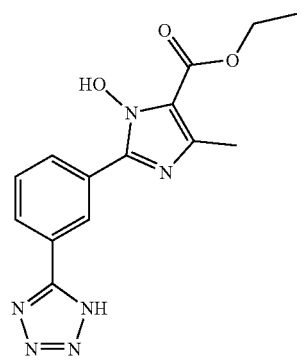

LY-15

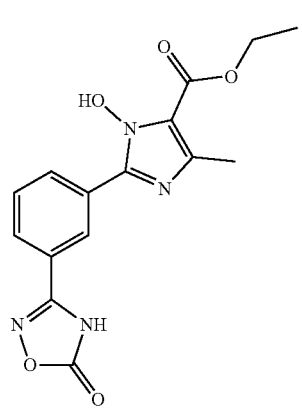

LY-16

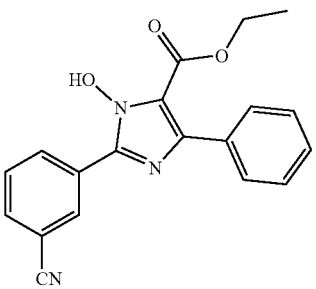

LY-19

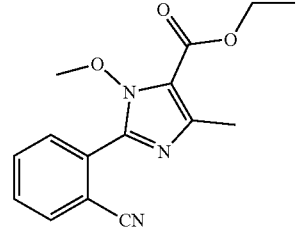

LY-22

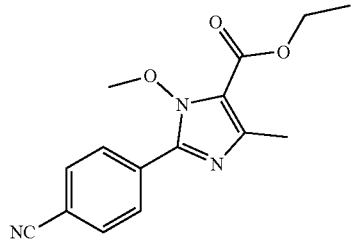

LY-25
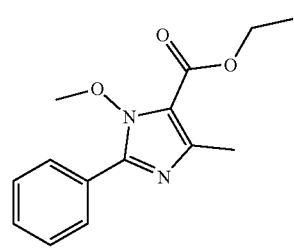
LY-26a
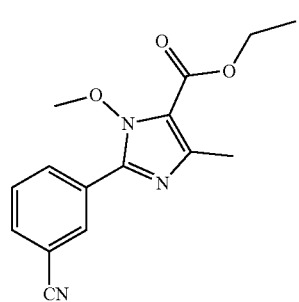
LY-26b
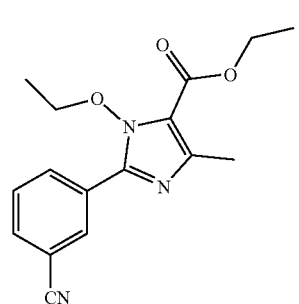
LY-26c
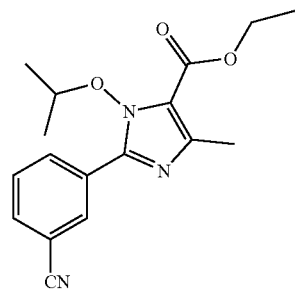
LY-26d
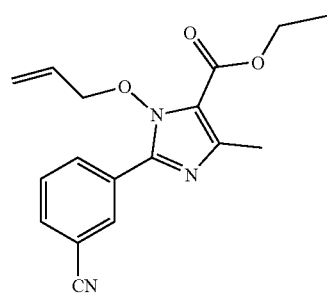
LY-26e
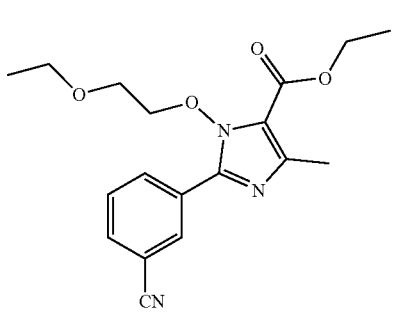
LY-26f
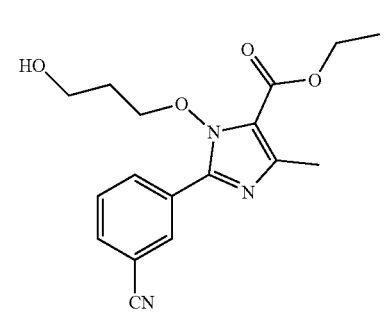
LY-26g
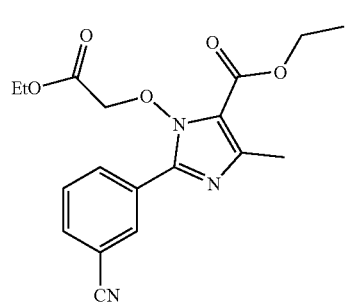
LY-26h
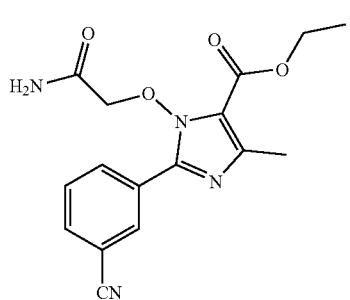
LY-26i
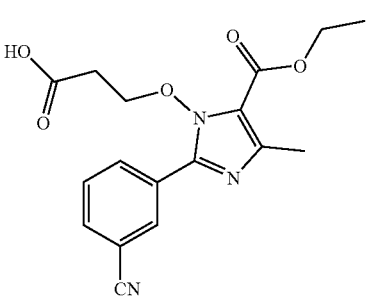

-continued
LY-26j
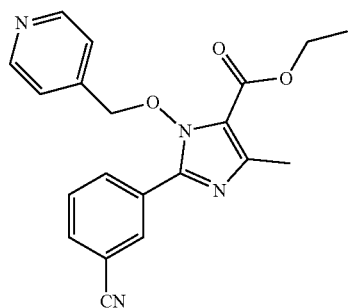
LY-26k
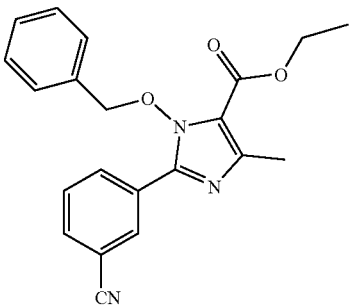
LY-26l
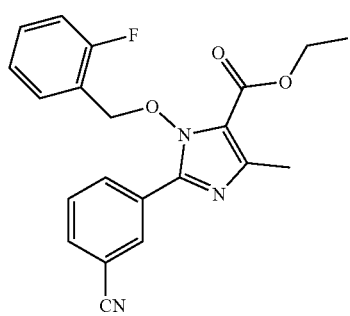
LY-26m
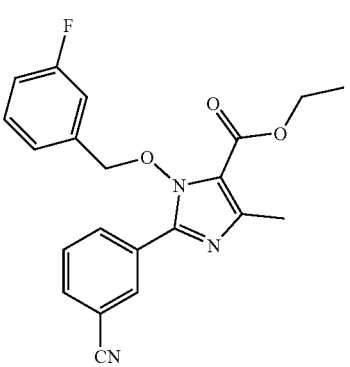
LY-26n
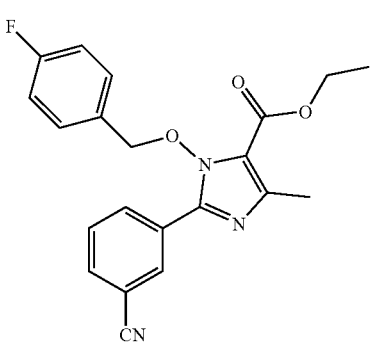
-continued
LY-26o
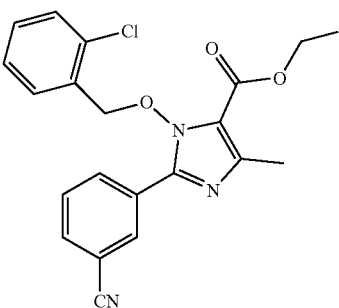
LY-26p
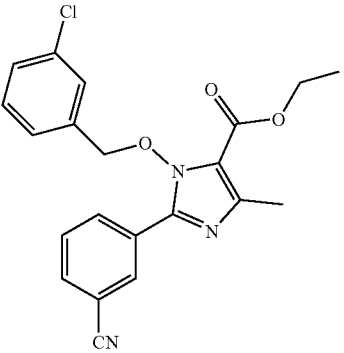
LY-26q
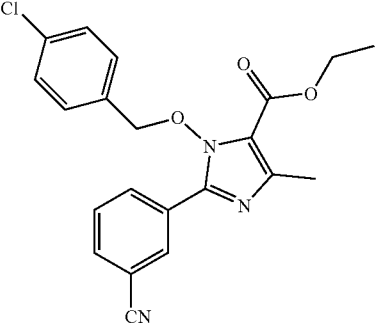
LY-26r
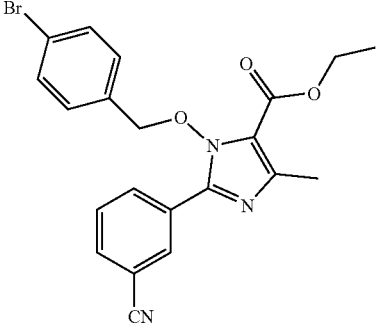

-continued
LY-26s
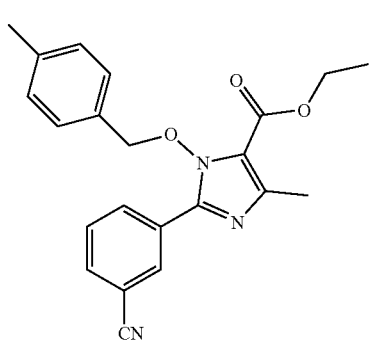
LY-26t
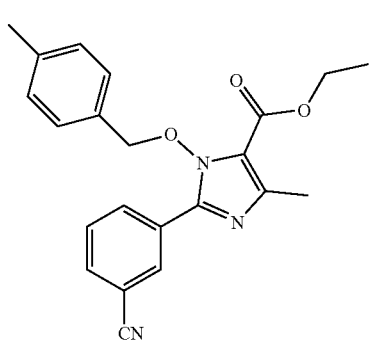
LY-26u
LY-26v
-continued
LY-26w
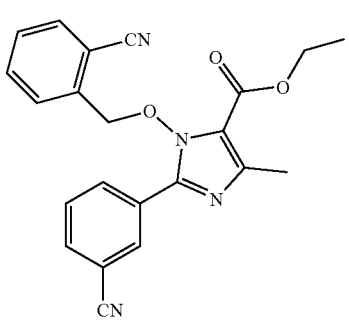
LY-26x
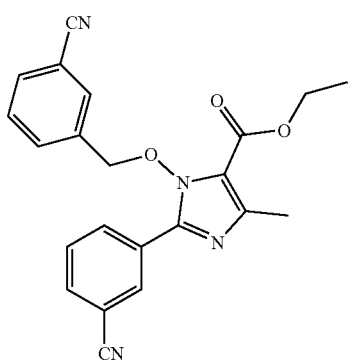
LY-26y
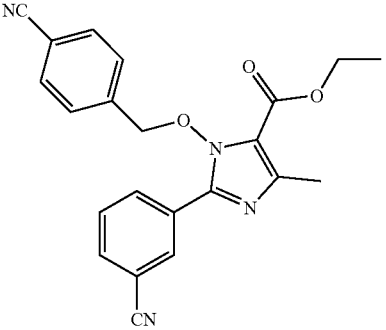
LY-11
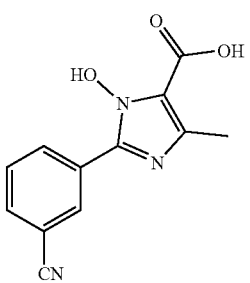
LY-27a
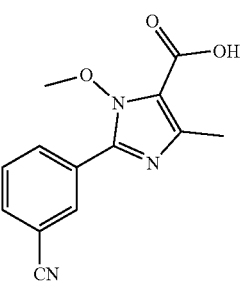

LY-27b
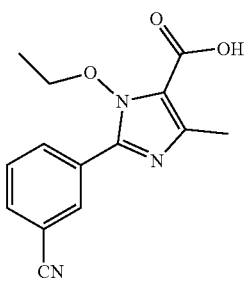
LY-27d
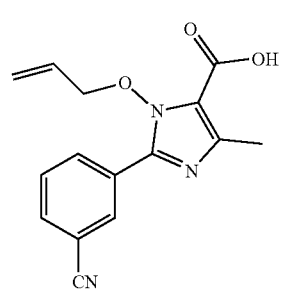
LY-27k
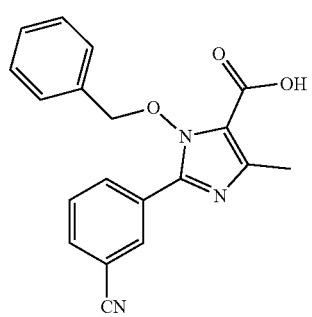
LY-27s
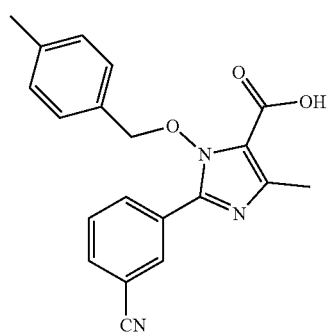
LY-27y
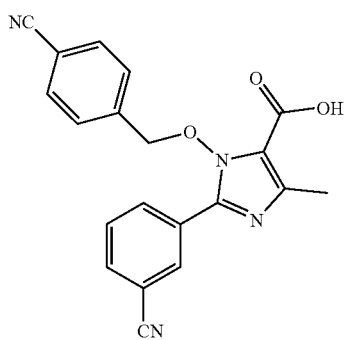
LY-28a
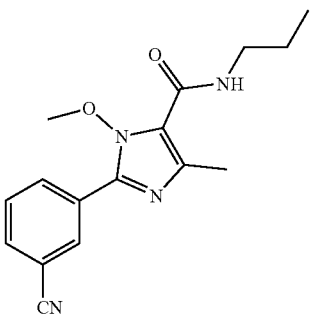
LY-28b
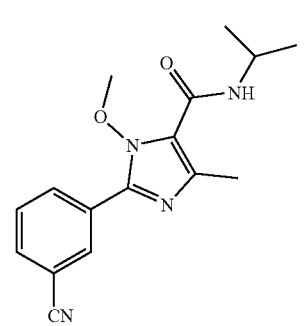
LY-28c
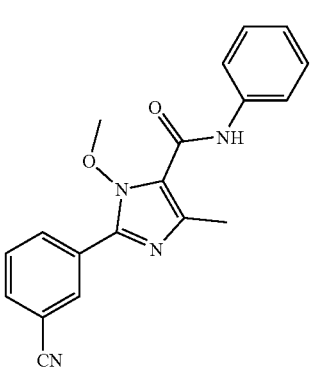
LY-30a
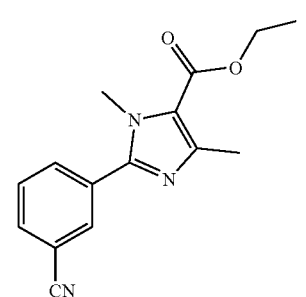
LY-F1
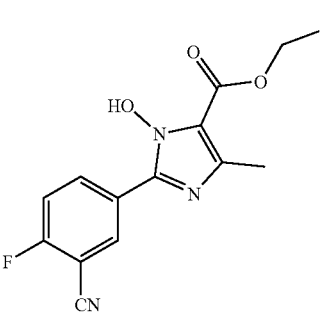

In a second aspect, this application further provides a method for preparing the compound of formula (I) or a pharmaceutically-acceptable salt thereof, comprising:

subjecting a substituted benzaldehyde and ethyl 2-hydroxyimino-3-oxobutyrate to cyclization reaction to obtain an intermediate ethyl 2-aryl-1-hydroxy-4-methyl-1H-imidazole-5-carboxylate; and subjecting the intermediate to alkylation with a halogenated hydrocarbon followed by hydrolysis or ammonolysis to produce the compound of formula (I).

In some embodiments, the method comprises:

(1) subjecting ethyl 3-oxobutyrate to nitrosation with sodium nitrite in acetic acid to obtain the intermediate ethyl 2-hydroxyimino-3-oxobutyrate; and (2) subjecting p-hydroxybenzaldehyde to bromination with bromine to obtain 3-bromo-4-hydroxybenzaldehyde; alkylating 3-bromo-4-hydroxybenzaldehyde with isobutyl bromide to obtain 3-bromo-4-isobutoxybenzaldehyde; reacting 3-bromo-4-isobutoxybenzaldehyde with cuprous cyanide in N,N-dimethylformamide to obtain 3-cyano-4-isobutoxybenzaldehyde; subjecting 3-cyano-4-isobutoxybenzaldehyde to cyclization reaction with ethyl 2-hydroxyimino-3-oxobutanoate under the catalysis of ammonium acetate in acetic acid to obtain intermediate ethyl 2-(3-cyano-4-isobutoxyphenyl)-1-hydroxy-4-methyl-1H-imidazole-5-carboxylate; reacting ethyl 2-(3-cyano-4-isobutoxyphenyl)-1-hydroxy-4-methyl-1H-imidazole-5-carboxylate with acetyl chloride in the presence of triethylamine to obtain ethyl 1-acetoxy-2-(3-cyano-4-isobutyloxyphenyl)-4-methyl-1H-imidazole-5-carboxylate (LY-8a).

In an embodiment, the method comprises:

subjecting compound LY-7b to reduction reaction with hydrogen under the catalysis of Pd/C in N,N-dimethylformamide to remove benzyl group to obtain the compound LY-8b.

In an embodiment, the method comprises:

cyclizing 3-cyanobenzaldehyde with ethyl 2-hydroxyimino-3-oxobutyrate under the catalysis of ammonium acetate in acetic acid to obtain ethyl 2-(3-cyanophenyl)-1-hydroxy-4-methyl-1H-imidazole-5-carboxylate (LY-10).

In an embodiment, the method comprises:

subjecting 3-cyanobenzaldehyde to cyclization reaction with sodium azide under the catalysis of copper sulfate in N,N-dimethylformamide to obtain 3-(5-oxo-4,5-dihydro-1,2,4-oxadiazol-3-yl)benzaldehyde; and subjecting 3-(5-oxo-4,5-dihydro-1,2,4-oxadiazol-3-yl)benzaldehyde to cyclization reaction with ethyl 2-hydroxyimino-3-oxobutyrate under the catalysis of ammonium acetate in acetic acid to obtain ethyl 2-[3-(1H-tetrazol-5-yl)phenyl]-1-hydroxy-4-methyl-1H-imidazole-5-carboxylate (LY-13).

In an embodiment, the method comprises:

reacting 3-cyanobenzaldehyde with hydroxylamine hydrochloride in the presence of potassium carbonate to obtain 3-formyl-N-hydroxybenzamidine; reacting 3-formyl-N-hydroxybenzamidine with N,N'-carbonyldiimidazole in the presence of 1,8-diazabicyclo[5.4.0]undec-7-ene under a basic condition to obtain 3-(5-oxo-4,5-dihydro-1,2,4-oxadiazol-3-yl) benzaldehyde; and subjecting 3-(5-oxo-4,5-dihydro-1,2,4-oxadiazol-3-yl) benzaldehyde to cyclization reaction with ethyl 2-hydroxyimino-3-oxobutyrate to obtain ethyl 1-hydroxy-4-methyl-2-[3-(5-oxo-4,5-dihydro-1,2,4-oxadiazol-3-yl)phenyl]-1H-imidazole-5-carboxylate (LY-15) under the catalysis of ammonium acetate in acetic acid.

In an embodiment, the method comprises:

subjecting 3-cyanobenzaldehyde to cyclization reaction with ethyl 2-hydroxyimino-3-oxo-3-phenylpropionate under the catalysis of ammonium acetate in acetic acid to obtain ethyl 2-(3-cyanophenyl)-1-hydroxy-4-phenyl-1H-imidazole-5-carboxylate (LY-16).

In an embodiment, the method comprises:

subjecting o-cyanobenzaldehyde to cyclization reaction with ethyl 2-hydroxyimino-3-oxo-3-phenylpropionate under the catalysis of ammonium acetate in acetic acid to obtain ethyl 2-(2-cyanophenyl)-1-hydroxy-4-methyl-1H-imidazole-5-carboxylate (LY-18); and reacting ethyl 2-(2-cyanophenyl)-1-hydroxy-4-methyl-1H-imidazole-5-carboxylate with dimethyl sulfate in the presence of potassium carbonate in N,N'-carbonyldiimidazole to obtain ethyl 2-(2-cyanophenyl)-1-methoxy-4-methyl-1H-imidazole-5-carboxylate (LY-19).

In an embodiment, the method comprises:

subjecting p-cyanobenzaldehyde to cyclization reaction with ethyl 2-hydroxyimino-3-oxo-3-phenylpropionate under the catalysis of ammonium acetate in acetic acid to obtain ethyl 2-(4-cyanophenyl)-1-hydroxy-4-methyl-1H-imidazole-5-carboxylate (LY-21); and reacting ethyl 2-(4-cyanophenyl)-1-hydroxy-4-methyl-1H-imidazole-5-carboxylate with dimethyl sulfate in the presence of potassium carbonate in N,N'-carbonyldiimidazole to obtain ethyl 2-(4-cyanophenyl)-1-methoxy-4-methyl-1H-imidazole-5-carboxylate (LY-22).

In an embodiment, the method comprises:

subjecting benzaldehyde to cyclization reaction with ethyl 2-hydroxyimino-3-oxo-3-phenylpropionate under the catalysis of ammonium acetate in acetic acid to obtain ethyl 1-hydroxy-4-methyl-2-phenyl-1H-imidazole-5-carboxylate (LY-24); and reacting ethyl 1-hydroxy-4-methyl-2-phenyl-1H-imidazole-5-carboxylate with dimethyl sulfate in the presence of potassium carbonate in N,N'-carbonyldiimidazole to obtain ethyl 1-methoxy-2,4-dimethyl-2-phenyl-1H-imidazole-5-carboxylate (LY-25).

In an embodiment, the method comprises:

subjecting ethyl 2-(3-cyanophenyl)-1-hydroxy-4-methyl-1H-imidazole-5-carboxylate (LY-10) to alkylation with a corresponding halogenated hydrocarbon to obtain ethyl 2-(3-cyanophenyl)-4-methyl-1-alkoxy-1H-imidazole-5-carboxylate (LY-26a-26y).

In an embodiment, the method comprises:

hydrolyzing ethyl 2-(3-cyanophenyl)-4-methyl-1-alkoxy-1H-imidazole-5-carboxylate (LY-26a, LY-26b, LY-26d, LY-26k, LY-26s or LY-26y) in the presence of lithium hydroxide in a mixture of tetrahydrofuran and water in a volume ratio of 1:1 to obtain 2-(3-cyanophenyl)-4-methyl-1-alkoxy-1H-imidazole-5-carboxylic acid (LY-27a, LY-27b, LY-27d, LY-27k, LY-27s or LY-27y); and subjecting the compound LY-26a to condensation with propylamine, isopropylamine or aniline under the catalysis of N,N'-carbonyldiimidazole/1,8-diazabicyclo[5.4.0]undec-7-ene to obtain 2-(3-cyanophenyl)-N-propyl-1-methoxy-4-methyl-1H-imidazole-5-carboxamide (LY-28a), 2-(3-cyanophenyl)-N-isopropyl-1-methoxy-4-methyl-1H-imidazole-5-carboxamide (LY-28b) or 2-(3-cyanophenyl)-1-methoxy-4-methyl-N-phenyl-1H-imidazole-5-carboxamide (LY-28c).

In an embodiment, the method comprises:

reacting LY-10 with trimethylchlorosilane and sodium iodide in acetonitrile under reflux to obtain ethyl 2-(3-cyanophenyl)-4-methyl-1H-imidazole-5-carboxylate (LY-29); and subjecting ethyl 2-(3-cyanophenyl)-4-methyl-1H-imidazole-5-carboxylate to alkylation with iodomethane in the presence of potassium carbonate in N,N-dimethylformamide to obtain ethyl 2-(3-cyanophenyl)-1,4-dimethyl-1H-imidazole-5-carboxylate (LY-30).

In an embodiment, the method comprises:

subjecting 2-fluoro-5-cyanobenzaldehyde to cyclization reaction with ethyl 2-hydroxyimino-3-oxo-3-phenylpropionate under the catalysis of ammonium acetate in acetic acid to obtain ethyl 2-(3-cyano-4-fluorophenyl)-1-hydroxy-4-methyl-1H-imidazole-5-carboxylate (LY-F1).

Several synthetic routes are illustrated as follows.

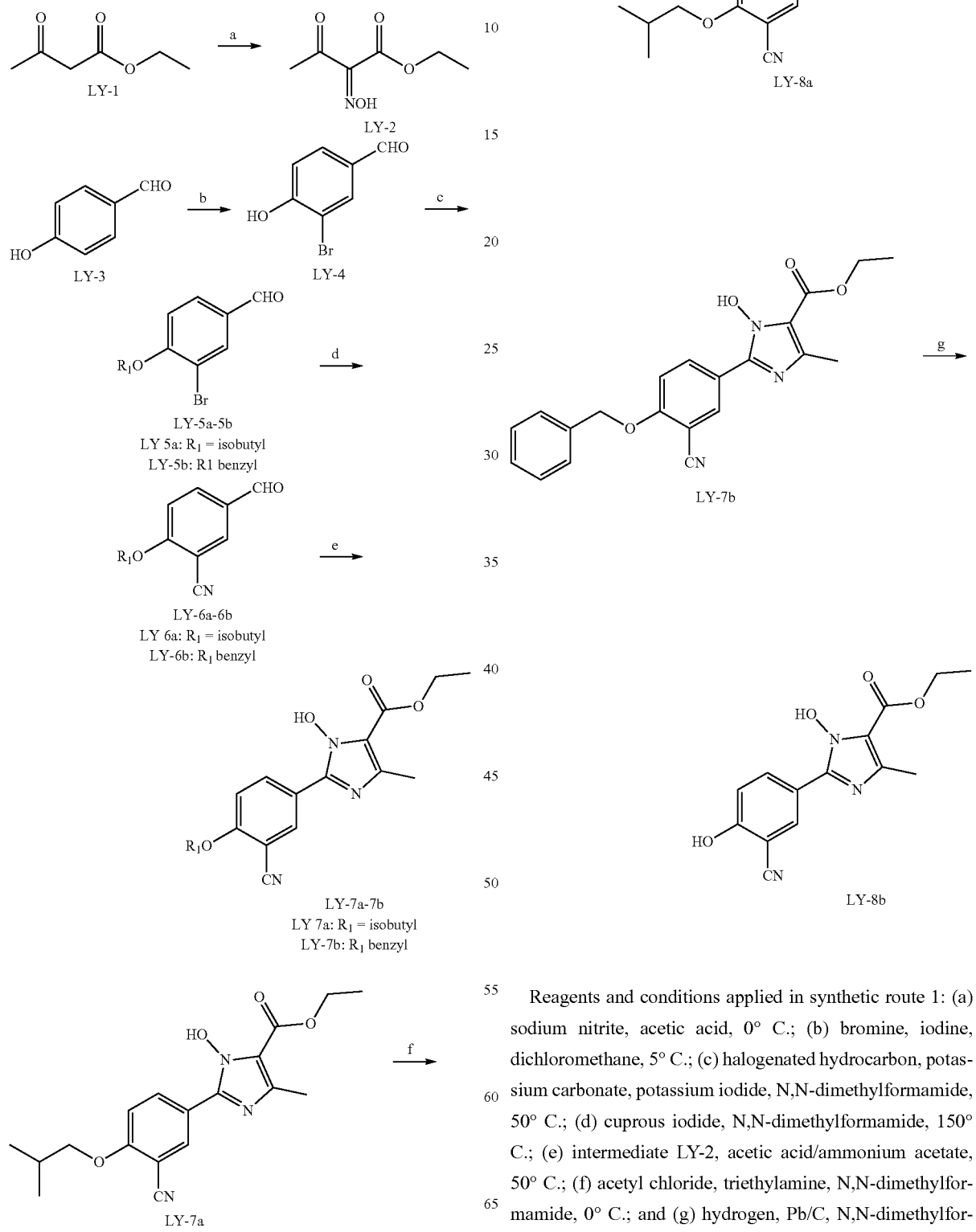

Reagents and conditions applied in synthetic route 1: (a) sodium nitrite, acetic acid, 0° C.; (b) bromine, iodine, dichloromethane, 5° C.; (c) halogenated hydrocarbon, potassium carbonate, potassium iodide, N,N-dimethylformamide, 50° C.; (d) cuprous iodide, N,N-dimethylformamide, 150° C.; (e) intermediate LY-2, acetic acid/ammonium acetate, 50° C.; (f) acetyl chloride, triethylamine, N,N-dimethylformamide, 0° C.; and (g) hydrogen, Pb/C, N,N-dimethylformamide, 25° C.

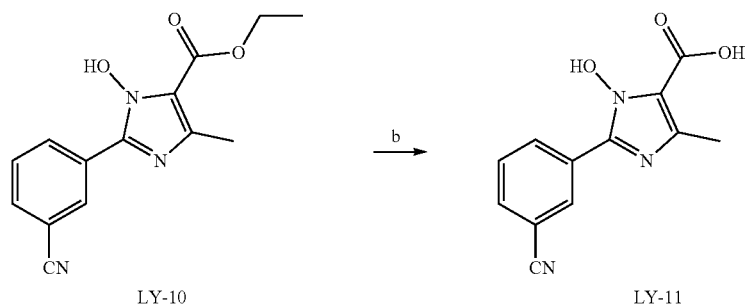
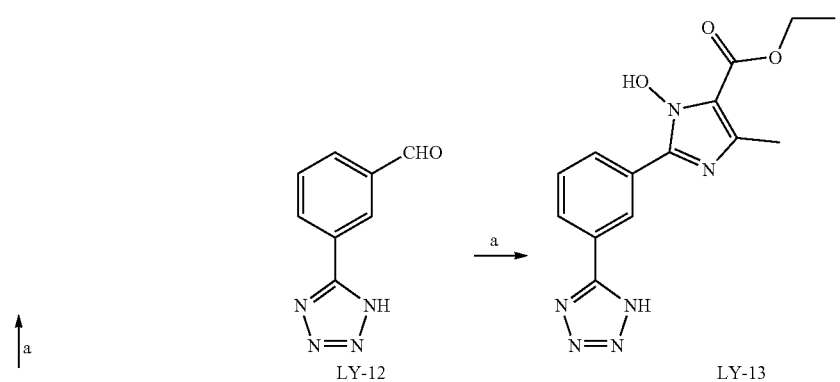
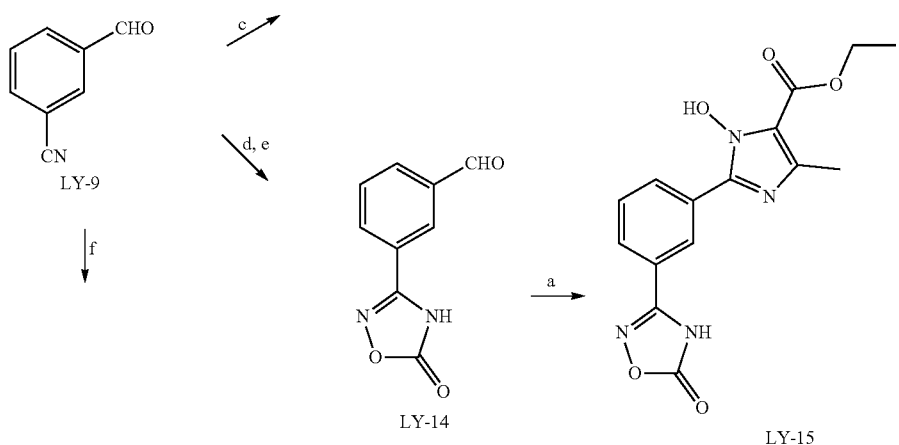
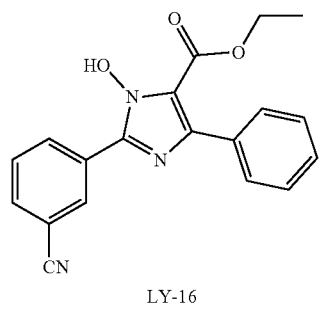

Reagents and conditions applied in synthetic route 2: (a) intermediate LY-2, acetic acid/ammonium acetate, 50° C.; (b) lithium hydroxide, tetrahydrofuran, water, 50° C.; (c) sodium azide, cuprous sulfate, N,N-dimethylformamide, 120° C.; (d) hydroxylamine hydrochloride, sodium carbonate, dimethyl sulfoxide, 80° C.; (e) N,N'-carbonyldiimidazole, 1,8-diazabicyclo[5.4.0]undec-7-ene, dichloromethane, 30° C.; and (f) ethyl (2Z)-2-hydroxyimino-3-oxo-3-phenylpropionate, acetic acid/ammonium acetate, 50° C.

LY-17

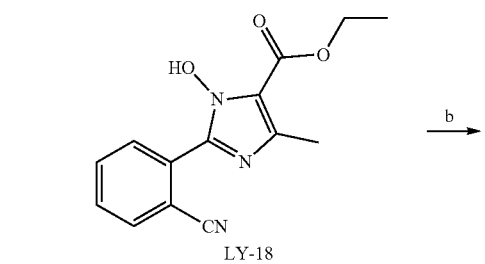

LY-18

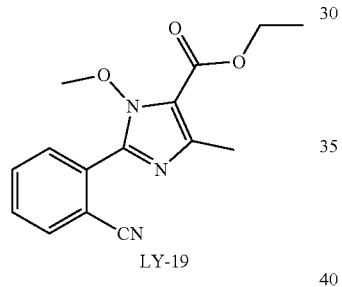

LY-19

Reagents and conditions applied in synthetic route 3: (a) intermediate LY-2, acetic acid/ammonium acetate, 50° C.; and (b) dimethyl sulfate, potassium carbonate, N,N-dimethylformamide, 0° C.

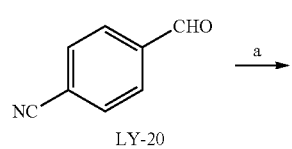

LY-20

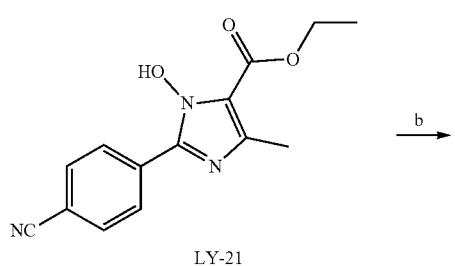

LY-21

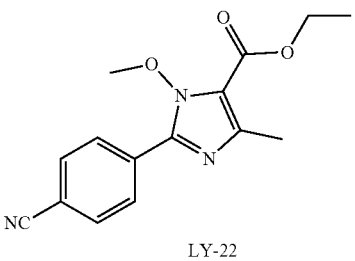

LY-22

Reagents and conditions applied in synthetic route 4: (a) intermediate LY-2, acetic acid/ammonium acetate, 50° C.; and (b) dimethyl sulfate, potassium carbonate, N,N-dimethylformamide, 0° C.

LY-23

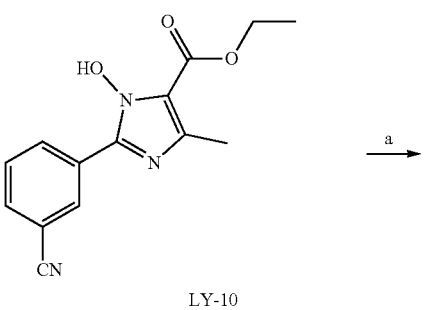

LY-24

LY-25

Reagents and conditions applied in synthetic route 5: (a) intermediate LY-2, acetic acid/ammonium acetate, 50° C.; and (b) dimethyl sulfate, potassium carbonate, N,N-dimethylformamide, 0° C.

LY-10

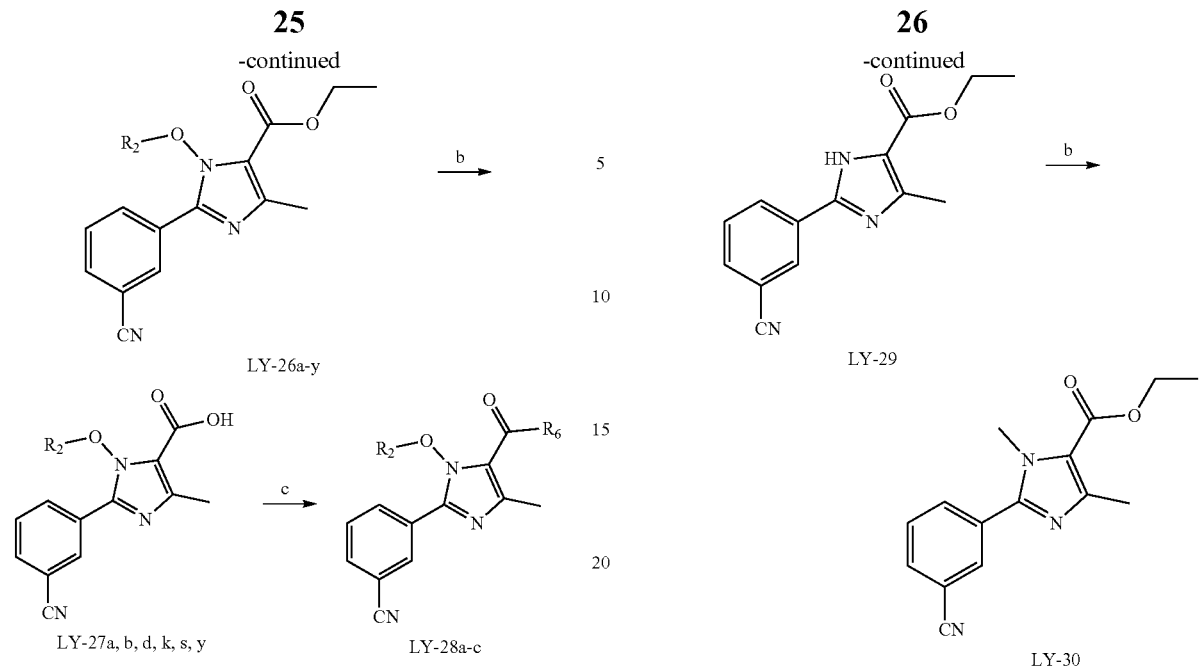

LY-26a: R₂ = methyl
LY-26b: R₂ = ethyl
LY-26c: R₂ = isobutyl
LY-26d: R₂ = allyl
LY-26e: R₂ = 2-ethoxyethyl
LY-26f: R₂ = 3-hydroxypropyl
LY-26g: R₂ = 2-ethoxy-2-oxoethyl
LY-26h: R₂ = 2-amino-2-oxoethyl
LY-26i: R₂ = 2-carboxyethyl
LY-26j: R₂ = pyridin-4-ylmethyl
LY-26k: R₂ = benzyl
LY-26l: R₂ = 2-fluorobenzyl LY-26m: R₂ = 3-fluorobenzyl
LY-26n: R₂ = 4-fluorobenzyl
LY-26o: R₂ = 2-chlorobenzyl
LY-26p: R₂ = 3-chlorobenzyl
LY-26q: R₂ = 4-chlorobenzyl
LY-26r: R₂ = 4-bromobenzyl
LY-26s: R₂ = 4-methylbenzyl
LY-26t: R₂ = 4-methoxybenzyl
LY-26u: R₂ = 4-(methoxycarbonyl)benzyl
LY-26v: R₂ = 4-nitrobenzyl
LY-26w: R₂ = 2-cyanobenzyl
LY-26x: R₂ = 3-cyanobenzyl LY-26y: R₂ = 4-cyanobenzyl
LY-27a: R₂ = methyl
LY-27b: R₂ = ethyl
LY-27d: R₂ = allyl
LY-27k: R₂ = benzyl
LY-27s: R₂ = 4-methylbenzyl
LY-27y-: R₂ = 4-cyanobenzyl
LY-28a: R₂ = methyl, R₆ = propylamino
LY-28b: R₂ = methyl, R₆ = isopropylamino
LY-28c: R₂ = methyl, R₆ = anilino Reagents and conditions applied in synthetic route 6: (a) halogenated hydrocarbon, potassium carbonate, potassium iodide, nitrogen, N,N-dimethylformamide, 0-50° C.; (b) lithium hydroxide, tetrahydrofuran, water, 50° C.; (c) benzotriazole-N,N,N',N'-tetramethylurea hexafluorophosphate, triethylamine, aliphatic amine or aniline, N,N-dimethylformamide.

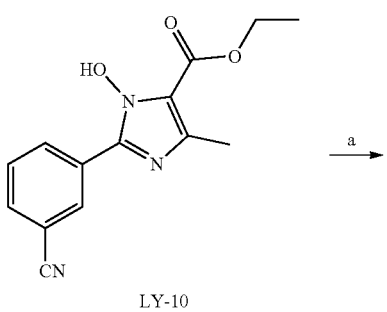

LY-10

Reagents and conditions applied in synthetic route 7: (a) trimethylchlorosilane, sodium iodide, acetonitrile, reflux; and (b) methyl iodide, potassium carbonate, nitrogen, N,N-dimethylformamide, 0-50° C.

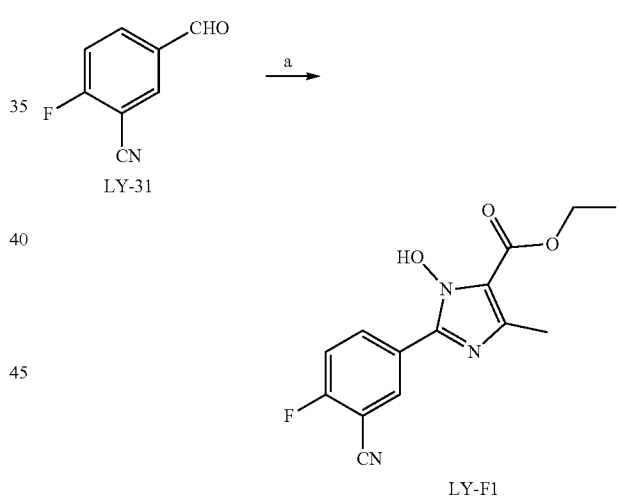

Reagents and conditions applied in synthetic route 8: (a) intermediate LY-2, acetic acid/ammonium acetate, 50° C.

In a third aspect, this application provides a pharmaceutical composition, comprising: the compound of formula (I) or a pharmaceutically-acceptable salt, an isomer, a polymorph, or a pharmaceutically-acceptable solvate thereof as an active ingredient, and a pharmaceutically-acceptable adjuvant, a carrier and a diluent.

In an embodiment, the pharmaceutical composition is prepared by a conventional method as described in *Remington: the Science and Practice of Pharmacy,* 19th, ED., 1995. The composition can be administered in the form of capsule, tablet, powder, solution, suspension, syrup or aerosol, or can be topically administered. The composition may contain a suitable solid or liquid carrier, or be prepared into an injection or a suspension in a suitable sterile medium. The composition may contain 0.5%-20%, preferably 5%-10%, by weight of the active compound, and a pharmaceutically-acceptable carrier, an excipient, a diluent and a solvent.

In an embodiment, the composition comprises the compound of formula (I) or a pharmaceutically-acceptable salt, an isomer, a polymorph or a pharmaceutically-acceptable solvate thereof, and a pharmaceutically-acceptable excipient, where the excipient can be a carrier or a diluent, or can be diluted by a carrier or packaged in a carrier. Moreover, the excipient can be in the form of a capsule, sachet, paper or solvent. The diluent can be a solid, semi-solid, or liquid substance and served as a carrier, excipient, or medium for the active compound. The active compound can be absorbed in the form of granular solid in a container such as a sachet. Suitable carriers exemplarily include water, salt solution, alcohol, polyethylene glycol, polyhydroxyethoxylated castor oil, peanut oil, olive oil, gelatin, lactose, gypsum powder, sucrose, cyclodextrin, amylose, stearin magnesium, talc, agar, pectin, gum arabic, lower alkyl ether of cellulose and stearic acid, silicic acid, fatty acid, aliphatic amide, fatty acid monoglyceride and diglyceride, pentaerythritol fatty acid ester, polyoxyethylene, hydroxymethyl cellulose and polyvinylpyrrolidone. Likewise, the carrier or diluent can be any delayed-release material in the prior art, such as glyceryl monostearate or glyceryl distearate, which can be used alone or in combination with wax. The composition can be formulated by a known method in the art to which this application pertains to achieve the rapid, sustained or delayed release of the active ingredient.

The pharmaceutical composition is sterile and can be mixed with adjuvants, emulsifiers, buffers and/or coloring agents if necessary, as long as these substances do not react with the active compound.

The pharmaceutical composition can be administered to the patients by any route as long as the active compound can be effectively delivered to the appropriate or desired site. The administration route includes oral administration, nasal administration, transdermal administration, pulmonary administration and parenteral administration. For example, the composition can be administered rectally, subcutaneously, intravenously, intraurethrally, intramuscularly or intranasally, or in the form of ophthalmic solutions or ointments. Preferably, the composition is administered by the oral route.

In an embodiment, the oral preparation containing a solid carrier can be pressed into tablets, or filled into capsules in the form of powder or pellets, or made into troches or lozenges. If a liquid carrier is used, the preparation may be a syrup, emulsion, soft gelatin capsule or sterile injection, such as an aqueous or non-aqueous suspension or solution.

The compound of formula (I) can be dissolved or suspended in a liquid carrier, preferably in an aqueous carrier, to produce an aerosol for intranasal administration. The carrier can contain additives including solubilizers such as propylene glycol, surfactants and absorption enhancers such as lecithin and cyclodextrin, and preservatives such as parabens. For parenteral administration, the compound of formula (I) can be dissolved or suspended in a liquid carrier, preferably in an aqueous solution of polyhydroxylated castor oil, to produce a solution or suspension injection.

Tablets, dragees or capsules containing talc and/or carbohydrate carriers or binders are particularly suitable for oral administration. Preferably, the carbohydrate carrier is lactose, corn starch, potato starch or a mixture thereof. When a sugared carrier is used, the composition can be prepared into syrup.

In a fourth aspect, this application further provides a drug for preventing and treating a thrombotic disease, comprising:

the compound of formula (I), a pharmaceutically-acceptable salt thereof or a pharmaceutical composition comprising the same.

BRIEF DESCRIPTION OF THE DRAWINGS

The FIGURE shows effect of LY-26y on arterial thrombosis in male SD rats.

DETAILED DESCRIPTION OF EMBODIMENTS

This application will be further described in detail with reference to embodiments. It should be understood that these embodiments are merely illustrative of the invention, and are not intended to limit the invention.

Example 1 Preparation of 3-bromo-4-hydroxybenzaldehyde (LY-4)

12.2 g (0.10 mol) of p-hydroxybenzaldehyde was added into 240 mL of dichloromethane to produce a mixture, which was then cooled to −5° C. in an ice bath. 16.8 g (0.105 mol) of bromine was diluted with 60 mL of dichloromethane and added dropwise to the mixture at 0° C. or less. The reaction mixture was reacted under stirring overnight at room temperature, added with a 0.9% sodium bisulfite solution and stirred until a large amount of white solid was precipitated. The reaction mixture was filtered under vacuum, and a filter cake was collected, rinsed twice with 100 mL of water, drained, and beaten with ethyl acetate to obtain 15.0 g of white solid with a yield of 75.1%.

MS(ESI) m/z: [M−H]⁻ 198.9.

Example 2 Preparation of 3-bromo-4-isobutyloxybenzaldehyde (LY-5a)

2 g (10 mmol) of 3-bromo-4-hydroxybenzaldehyde and 1.67 g (12 mmol) of anhydrous potassium carbonate were added into 10 mL of N,N-dimethylformamide. The reaction mixture was stirred for 15 min, and added with 1.64 g (12 mmol) of isobutyl bromide. The reaction mixture was reacted at room temperature under stirring for 1 h, and added with 20 mL of water to precipitate a large amount of grayish white solid. The reaction mixture was filtered, and a filter cake was collected, rinsed twice with 10 mL of water and drained to obtain a crude product, which was directly used in the next reaction without purification.

Example 3 Preparation of 3-bromo-4-benzyloxybenzaldehyde (LY-5b)

The preparation in this example was basically the same as that of Example 2 except that the starting material used herein was benzyl chloride, and a white solid was obtained with a yield of 68.3%.

$^1$H NMR (400 MHz, DMSO-$d_6$): δ 9.85 (s, 1H), 8.11 (d, J=2.0 Hz, 1H), 7.91 (dd, J=8.5, 2.0 Hz, 1H), 7.53-7.47 (m, 2H), 7.45-7.38 (m, 3H), 7.38-7.34 (m, 1H), 5.34 (s, 2H).

Example 4 Preparation of 3-cyano-4-isobutoxybenzaldehyde (LY-6a)

8 mmol of 4-isobutoxy-3-bromobenzaldehyde (LY-5a), 8.8 mmol of cuprous cyanide and 10 mL of N,N-dimethylformamide were mixed and reacted at 150° C. under the protection of nitrogen for 8 h. After the reaction was completed, the reaction mixture was cooled to room temperature and diluted with dichloromethane. The reaction mixture was filtered to remove insoluble components, and the filtrate was collected, washed sequentially with ammonia water, water, and saturated brine, dried with anhydrous sodium sulfate and evaporated to remove solvent to obtain a solid. The solid was beaten with ethyl acetate to obtain a white solid, which was directly used in the next reaction without purification.

Example 5 Preparation of 3-cyano-4-benzyloxybenzaldehyde (LY-6b)

The preparation in this example was basically the same as that of Example 4 except that the starting material was LY-5b, and a white solid was obtained with a yield of 72.3%.

$^1$H NMR (400 MHz, DMSO-$d_6$): δ 9.89 (s, 1H), 8.30 (d, J=2.1 Hz, 1H), 8.17 (dd, J=8.8, 2.1 Hz, 1H), 7.54 (d, J=8.9 Hz, 1H), 7.52-7.48 (m, 2H), 7.48-7.40 (m, 2H), 7.40-7.32 (m, 1H), 5.41 (s, 2H).

Example 6 Preparation of ethyl 2-(3-cyano-4-isobutyloxy)phenyl-1-hydroxy-4-methyl-1H-imidazole-5-carboxylate (LY-7a)

43 mmol of 2-isobutoxy-5-formylbenzaldehyde (LY-6a), 52 mmol of ethyl 2-hydroxyimino-3-oxobutanoate and 430 mmol of ammonium acetate were mixed in 176 mL of acetic acid and reacted under stirring at 50° C. for 24 h. After the reaction was completed, the reaction mixture was cooled to room temperature and poured slowly into 500 mL of cold water. The reaction mixture was filtered, and a filter residue was collected and dried to obtain a white solid, which was directly used in the next reaction without purification.

Example 7 Preparation of ethyl 2-(3-cyano-4-benzyloxy)phenyl-1-hydroxy-4-methyl-1H-imidazole-5-carboxylate (LY-7b)

The preparation in this example was basically the same as that of Example 6 except that the starting material was LY-6b, and the obtained crude product was directly used in the next reaction without purification.

Example 8 Preparation of ethyl 1-acetoxy-2-(3-cyano-4-isobutoxyphenyl)-4-methyl-1H-imidazole-5-carboxylate (LY-8a)

30 mmol of LY-7a, 15 mmol of triethylamine and 150 mL of dichloromethane were stirred at 0° C. for 5 min, to which 30 mmol of acetyl chloride was added dropwise for reaction. The reaction mixture was washed with 150 mL of water twice and evaporated to obtain a solid. The solid was beaten with ethyl acetate to obtain a white solid with a yield of 83.3% (Mp 112.3° C.-113.2° C.).

ESI-HRMS calcd. for $C_{20}H_{23}N_3O_5$ [M+H]$^+$ 386.1710, found: 386.1741.

$^1$H NMR (400 MHz, DMSO-$d_6$): δ 8.08-8.02 (m, 2H), 7.34 (d, J=8.9 Hz, 1H), 4.26 (q, J=7.4 Hz, 2H), 3.96 (d, J=6.5 Hz, 2H), 2.43 (s, 3H), 2.42 (s, 3H), 2.15-2.01 (m, J=6.6 Hz, 1H), 1.29 (t, J=7.1 Hz, 3H), 1.01 (d, J=6.7 Hz, 6H).

$^{13}$C NMR (100 MHz, DMSO-$d_6$): δ 168.38, 161.70, 158.66, 143.58, 141.75, 134.09, 132.74, 120.01, 115.80, 114.20, 101.97, 75.47, 60.95, 26.02, 19.11, 18.29, 16.02, 14.48.

Example 9 Preparation of ethyl 2-(3-cyano-4-hydroxyphenyl)-1-hydroxy-4-methyl-1H-imidazole-5-carboxylate (LY-8b)

30 mmol of LY-7b, 900 mg of Pb/C and 40 mL of N,N-dimethylformamide were mixed and stirred at 25° C. in hydrogen for 2 h. The reaction mixture was filtered to remove insoluble components, and the filtrate was poured into water and then filtered under vacuum to collect a filter cake. The filter cake was washed twice with water and beaten with ethyl acetate to obtain a white solid with a yield of 79.1% (Mp 174.6° C.-175.3° C.).

ESI-HRMS calcd. for $C_{14}H_{13}N_3O_4$ [M+H]$^+$ 268.0979, found: 268.1011.

$^1$H NMR (400 MHz, DMSO-$d_6$): δ 8.20 (d, J=2.2 Hz, 1H), 8.10 (dd, J=8.9, 2.2 Hz, 1H), 7.07 (d, J=8.9 Hz, 1H), 4.24 (q, J=7.0 Hz, 2H), 2.32 (s, 3H), 1.29 (t, J=7.1 Hz, 3H).

$^{13}$C NMR (100 MHz, DMSO-$d_6$): δ 161.71, 159.46, 142.10, 141.47, 134.16, 132.35, 120.06, 118.21, 117.18, 117.01, 99.49, 60.16, 16.05, 14.64.

Example 10 Preparation of ethyl 2-(3-cyanophenyl)-1-hydroxy-4-methyl-1H-imidazole-5-carboxylate (LY-10)

The preparation in this example was basically the same as that of Example 6 except that the starting material was m-cyanobenzaldehyde, and a white solid was obtained with a yield of 68.2% (Mp 167.7° C.-170.2° C.).

ESI-HRMS calcd. for $C_{14}H_{13}N_3O_3$ [M+H]$^+$ 272.1030, found: 272.1057.

$^1$H NMR (400 MHz, DMSO-$d_6$): δ 12.26 (s, 1H), 8.39 (t, J=1.7 Hz, 1H), 8.34 (dt, J=8.1, 1.4 Hz, 1H), 7.91 (dt, J=7.8, 1.4 Hz, 1H), 7.71 (t, J=7.9 Hz, 1H), 4.30 (q, J=7.1 Hz, 2H), 2.39 (s, 3H), 1.32 (t, J=7.1 Hz, 3H).

$^{13}$C NMR (100 MHz, DMSO-$d_6$): δ 159.33, 142.72, 141.14, 133.16, 132.35, 131.03, 130.49, 129.77, 118.94, 118.83, 112.29, 60.53, 16.14, 14.67.

Example 11 Preparation of 2-(3-cyanophenyl)-1-hydroxy-4-methyl-1H-imidazole-5-carboxylic acid (LY-11)

500 mg of LY-10, 200 mg of lithium hydroxide, 3 mL of water and 3 mL of tetrahydrofuran were added into a 25 mL single-neck bottle and then reacted at 50° C. for 8 h. Then the reaction mixture was added with 5 mL of water, cooled to room temperature and adjusted to pH 1 with a 1 M aqueous hydrochloric acid solution. The reaction mixture was stirred at room temperature for 30 min and then filtered under vacuum to collect a filter cake. The filter cake was washed twice with a small amount of tetrahydrofuran, subjected to hot beating with tetrahydrofuran and filtered under vacuum to obtain a white solid with a yield of 69.7%.

$^1$H NMR (400 MHz, DMSO-$d_6$): δ 12.26 (s, 1H), 8.39 (t, J=1.7 Hz, 1H), 8.34 (dt, J=8.1, 1.4 Hz, 1H), 7.91 (dt, J=7.8, 1.4 Hz, 1H), 7.71 (t, J=7.9 Hz, 1H), 4.30 (q, J=7.1 Hz, 2H), 2.39 (s, 3H), 1.32 (t, J=7.1 Hz, 3H).

$^{13}$C NMR (100 MHz, DMSO-$d_6$): δ 160.50, 133.92, 133.62, 131.57, 130.97, 130.66, 130.03, 125.22, 118.51, 118.42, 112.48, 11.49.

Example 12 Preparation of 3-(5H-tetrazol-5-yl)benzaldehyde (LY-12)

30 mmol of 3-cyanobenzaldehyde was dissolved into 40 mL of N,N-dimethylformamide under stirring, to which 60 mmol of copper sulfate was added. The reaction mixture was stirred for 15 min, added with 36 mmol of sodium azide and reacted at room temperature under stirring for 24 h. After the reaction was completed, the reaction mixture was added with 80 mL of dichloromethane and 80 mL of for extraction, and an organic layer was collected and evaporated to obtain a white solid 3-(5H-tetrazol-5-yl)benzaldehyde with a yield of 77.32%.

$^1$H NMR (400 MHz, DMSO-d$_6$): δ 10.13 (s, 1H), 8.56 (s, 1H), 8.35 (dt, J=7.8, 1.5 Hz, 1H), 8.12 (dt, J=7.7, 1.4 Hz, 1H), 7.85 (t, J=7.7 Hz, 1H).

Example 13 Preparation of ethyl 2-[3-(1H-tetrazol-5-yl)phenyl]-1-hydroxy-4-methyl-1H-imidazole-5-carboxylate (LY-13)

The preparation was basically the same as that of Example 6 except that the starting material was LY-12, and a white solid was obtained with a yield of 83.1% (Mp 176.3° C.-178.4° C.).

ESI-HRMS calcd. for $C_{14}H_{14}N_6O_3$ [M+H]$^+$ 315.1200, found: 315.1196.

$^1$H NMR (600 MHz, DMSO-d$_6$): δ 8.78 (s, 1H), 8.23 (d, J=7.8 Hz, 1H), 8.08 (d, J=7.7 Hz, 1H), 7.66 (t, J=7.8 Hz, 1H), 7.20 (s, 1H), 4.26 (q, J=7.1 Hz, 2H), 2.40 (s, 3H), 1.30 (t, J=7.1 Hz, 3H).

$^{13}$C NMR (150 MHz, DMSO-d$_6$): δ 159.44, 156.86, 142.56, 142.23, 129.94, 129.60, 129.55, 127.82, 126.68, 126.34, 118.67, 60.38, 16.14, 14.66.

Example 14 Preparation of 3-(5-oxo-4,5-dihydro-1,2,4-oxadiazol-3-yl)benzaldehyde (LY-14)

30 mmol of 3-cyanobenzaldehyde was reacted with 36 mmol of hydroxylamine hydrochloride in an alkaline environment under stirring for 30 min. After the reaction was completed, the reaction mixture was subjected to extraction with dichloromethane and water, and an organic phase was collected, added with 36 mmol of N,N'-carbonyl diimidazole and reacted under stirring for 18 h. The reaction mixture was washed with water and evaporated to dryness to obtain a white powder 3-(5-oxo-4,5-dihydro-1,2,4-oxadiazol-3-yl)benzaldehyde, which was directly used in the subsequent reaction without purification.

Example 15 Preparation of ethyl 1-hydroxy-4-methyl-2-[3-(5-oxo-4,5-dihydro-1,2,4-oxadiazol-3-yl)phenyl]-1H-imidazole-carboxylate (LY-15)

The preparation was basically the same as that of Example 6 except that the starting material was 3-(5-oxo-4,5-dihydro-1,2,4-oxadiazol-3-yl)benzaldehyde (LY-14), and a white solid was obtained with a yield of 65.5% (Mp 208.7° C.-210.3° C.).

ESI-HRMS calcd. for $C_{15}H_{14}N_4O_5$ [M+H]$^+$ 331.1037, found: 331.1066.

$^1$H NMR (400 MHz, DMSO-d$_6$): δ 12.49 (s, 1H), 8.53 (t, J=1.7 Hz, 1H), 8.29 (dt, J=7.9, 1.4 Hz, 1H), 7.85 (dt, J=7.9, 1.4 Hz, 1H), 7.70 (t, J=7.7 Hz, 1H), 4.30 (q, J=7.1 Hz, 2H), 2.40 (s, 3H), 1.32 (t, J=7.1 Hz, 3H).

$^{13}$C NMR (100 MHz, DMSO-d$_6$): δ 160.42, 159.38, 157.63, 142.65, 141.84, 131.17, 130.07, 129.64, 127.22, 125.48, 124.31, 118.75, 60.46, 16.12, 14.67.

Example 16 Preparation of ethyl 2-(3-cyanophenyl)-1-hydroxy-4-phenyl-1H-imidazole-5-carboxylate (LY-16)

43 mmol of m-cyanobenzaldehyde, 52 mmol of ethyl 2-hydroxyimino-3-oxo-3-phenylpropionate, 430 mmol of ammonium acetate and 176 mL acetic acid were mixed and reacted under stirring at 50° C. for 24 h. The reaction mixture was cooled to room temperature and poured slowly into 500 mL of cold water. The reaction mixture was filtered to collect a precipitate which was dried and recrystallized with N,N-dimethylformamide/water to obtain a white solid with a yield of 76.6% (Mp 130.5° C.-131.9° C.).

ESI-HRMS calcd. for $C_{19}H_{15}N_3O_3$ [M+H]$^+$ 334.1186, found: 334.1216.

$^1$H NMR (400 MHz, DMSO-d$_6$): δ 12.52 (s, 1H), 8.48 (s, 1H), 8.43 (d, J=8.2 Hz, 1H), 7.95 (d, J=7.4 Hz, 1H), 7.79-7.70 (m, 3H), 7.53-7.32 (m, 3H), 4.29 (q, J=7.1 Hz, 2H), 1.22 (t, J=7.1 Hz, 3H).

$^{13}$C NMR (100 MHz, DMSO-d$_6$): δ 159.47, 142.26, 141.75, 133.98, 133.37, 132.55, 131.30, 130.54, 129.70, 129.06, 126.58, 126.25, 119.56, 112.39, 61.21, 14.31.

Example 17 Preparation of ethyl 4-methyl-2-(2-cyanophenyl)-1-hydroxy-1H-imidazole-5-carboxylate (LY-18)

The preparation was basically the same as that of Example 6 except that the starting material was 2-cyanobenzaldehyde. The resulting crude product was directly used in the subsequent reaction without purification.

Example 18 Preparation of ethyl 4-methyl-2-(2-cyanophenyl)-1-methoxy-1H-imidazole-5-carboxylate (LY-19)

50 mmol of LY-18 prepared in Example 17, 75 mmol of potassium carbonate and 40 mL of N,N-dimethylformamide were stirred at 25° C. for 5 min. Then the reaction mixture was dropwise added with 53 mmol of dimethyl sulfate and stirred for 1.5 h. The reaction mixture was poured into 100 mL of ice water followed by stirring, and a solid was precipitated, collected, dried and recrystallized with ethyl acetate to obtain a white solid with a yield of 78.3% (Mp 144.2° C.-145.6° C.).

MS (ESI) m/z: 286.17 [M+H]$^+$.

$^1$H NMR (400 MHz, DMSO-d$_6$): δ 7.68-7.57 (m, 3H), 7.52 (dd, J=7.4, 1.4 Hz, 1H), 4.32 (q, J=7.1 Hz, 2H), 3.79 (s, 3H), 2.42 (s, 3H), 1.33 (t, J=7.1 Hz, 3H).

$^{13}$C NMR (100 MHz, DMSO-d$_6$): δ 158.69, 143.83, 140.26, 133.76, 132.12, 130.90, 130.81, 129.04, 118.69, 116.98, 112.71, 67.64, 60.83, 16.21, 14.53.

Example 19 Preparation of ethyl 4-methyl-2-(4-cyanophenyl)-1-hydroxy-1H-imidazole-5-carboxylate (LY-21)

The preparation was basically the same as that of Example 6 except that the starting material was p-cyanobenzaldehyde, and a white solid was obtained with a yield of 85.3%.

$^1$H NMR (400 MHz, DMSO-d$_6$): δ 12.36 (s, 1H), 8.22 (d, J=8.4 Hz, 2H), 7.93 (d, J=8.4 Hz, 2H), 4.29 (q, J=7.1 Hz, 2H), 2.38 (s, 3H), 1.31 (t, J=7.1 Hz, 3H).

Example 20 Preparation of ethyl 4-methyl-2-(4-cyanophenyl)-1-methoxy-1H-imidazole-5-carboxylate (LY-22)

The preparation in this example was basically the same as that of Example 18 except that the starting material was LY-21, and a white solid was obtained with a yield of 78.2% (Mp 147.3° C.-148.5° C.).

ESI-HRMS calcd. for $C_{15}H_{15}N_3O_3$ [M+H]$^+$ 266.1186, found: 266.1208.

$^1$H NMR (400 MHz, DMSO-d$_6$): δ 8.21 (dd, 2H), 7.99 (dd, 2H), 4.33 (q, J=7.1 Hz, 2H), 3.98 (s, 3H), 2.42 (s, 3H), 1.34 (t, J=7.1 Hz, 3H).

$^{13}$C NMR (100 MHz, DMSO-d$_6$): δ 158.67, 143.97, 140.37, 133.37, 131.94, 126.22, 118.88, 117.29, 112.53, 67.72, 60.90, 16.26, 14.55.

Example 21 Preparation of ethyl 4-methyl-2-phenyl-1-hydroxy-1H-imidazole-5-carboxylate (LY-24)

The preparation in this example was basically the same as that of Example 6 except that the starting material was benzaldehyde, and a white solid was obtained with a yield of 83.7% (Mp 131.5° C.-133.1° C.).

MS (ESI) m/z: 247.1 [M+H]$^+$.

$^1$H NMR (400 MHz, DMSO-d$_6$): δ 8.22-8.13 (m, 2H), 7.46-7.33 (m, 3H), 4.23 (q, J=7.1 Hz, 2H), 2.34 (s, 3H), 1.28 (t, J=7.1 Hz, 3H).

Example 22 Preparation of ethyl 4-methyl-2-phenyl-1-methoxy-1H-imidazole-5-carboxylate (LY-25)

The preparation was basically the same as that of Example 18 except that the starting material was LY-24, and a white solid was obtained with a yield of 76.2% (Mp 98.8° C.-100.4° C.).

ESI-HRMS calcd. for $C_{14}H_{16}N_2O_3$ [M+H]$^+$ 261.1234, found: 261.1300.

$^1$H NMR (600 MHz, DMSO-d$_6$): δ 8.10-7.99 (m, 2H), 7.57-7.45 (m, 3H), 4.30 (q, J=7.1 Hz, 2H), 3.93 (s, 3H), 2.40 (s, 3H), 1.32 (t, J=7.1 Hz, 3H).

$^{13}$C NMR (100 MHz, DMSO-d$_6$): δ 158.84, 143.68, 142.27, 130.39, 129.36, 127.95, 127.72, 116.35, 67.21, 60.62, 16.26, 14.57.

Example 23 Preparation of ethyl 2-(3-cyanophenyl)-1-methoxy-4-methyl-1H-imidazole-5-carboxylate (LY-26a)

21.4 mmol of LY-10, 25.7 mmol of methyl iodide, 42.7 mmol of anhydrous potassium carbonate and 32 mL of N,N-dimethylformamide were added into a 100 mL single-necked flask and reacted at 50° C. under the protection of nitrogen for 5 h. The reaction mixture was poured into 200 mL of ice water and stirred for 30 min, and then filtered under vacuum to collect a filter cake. The filter cake was washed twice with water, dried, recrystallized with a mixture of petroleum ether and ethyl acetate in a volume ratio of 2:1 and filtered under vacuum at room temperature. A filter cake was collected, washed twice with a small amount of petroleum ether and dried to obtain a white solid with a yield of 76.4% (Mp 122.4° C.-123.5° C.).

ESI-HRMS calcd. for $C_{15}H_{15}N_3O_3$ [M+H]$^+$ 265.1186, found: 266.1207.

$^1$H NMR (400 MHz, DMSO-d$_6$): δ 8.37-8.27 (m, 2H), 7.97 (dt, J=7.6, 1.4 Hz, 1H), 7.75 (t, J=7.8 Hz, 1H), 4.32 (q, J=7.1 Hz, 2H), 3.98 (s, 3H), 2.40 (s, 3H), 1.33 (t, J=7.1 Hz, 3H).

$^{13}$C NMR (100 MHz, DMSO-d$_6$): δ 158.68, 143.82, 140.26, 133.78, 132.14, 130.90, 130.82, 129.02, 118.70, 116.97, 112.70, 67.65, 60.84, 16.23, 14.54.

Example 24 Preparation of ethyl 2-(3-cyanophenyl)-1-ethoxy-4-methyl-1H-imidazole-5-carboxylate (LY-26b)

21.4 mmol of LY-10, 25.7 mmol of bromoethane, 42.7 mmol of anhydrous potassium carbonate, 4.26 mmol of potassium iodide and 32 mL of N,N-dimethylformamide were added into a 100 mL single-necked flask and then reacted at 50° C. under the protection of nitrogen for 5 h. The reaction mixture was poured into 200 mL of ice water and stirred for 30 min, and then filtered under vacuum to collect a filter cake. The filter cake was washed twice with water, dried, recrystallized with a mixture of petroleum ether and ethyl acetate in a volume ratio of 2:1 and filtered under vacuum at room temperature. A filter cake was collected, washed twice with a small amount of petroleum ether and dried to obtain a white solid with a yield of 80.2% (Mp 98.5° C.-99.4° C.).

ESI-HRMS calcd. for $C_{16}H_{17}N_3O_3$ [M+H]$^+$ 300.1343, found: 300.1360.

$^1$H NMR (400 MHz, DMSO-d$_6$): δ 8.37-8.26 (m, 2H), 7.96 (dt, J=7.8, 1.3 Hz, 1H), 7.75 (td, J=7.8, 0.8 Hz, 1H), 4.31 (q, J=7.1 Hz, 2H), 4.16 (q, J=7.0 Hz, 2H), 2.40 (s, 3H), 1.33 (t, J=7.1 Hz, 3H), 1.23 (t, J=7.0 Hz, 3H).

$^{13}$C NMR (100 MHz, DMSO-d$_6$): δ 158.77, 143.84, 140.61, 133.68, 132.11, 131.01, 130.81, 129.23, 118.67, 117.19, 112.60, 76.26, 60.81, 16.22, 14.55, 13.40.

Example 25 Preparation of ethyl 2-(3-cyanophenyl)-1-isopropoxy-4-methyl-1H-imidazole-5-carboxylate (LY-26c)

The preparation in this example was basically the same as that of Example 24 except that the halogenated compound used herein was isobutyl bromide, and a white solid was obtained with a yield of 84.2% (Mp 99.6° C.-101.5° C.).

ESI-HRMS calcd. for $C_{17}H_{19}N_3O_3$ [M+H]$^+$ 314.1499, found: 314.1513.

$^1$H NMR (600 MHz, DMSO-d$_6$): δ 8.31 (t, J=1.7 Hz, 1H), 8.29 (dt, J=8.0, 1.4 Hz, 1H), 7.95 (dt, J=7.8, 1.4 Hz, 1H), 7.74 (t, J=7.9 Hz, 1H), 4.44 (h, J=6.2 Hz, 1H), 4.31 (q, J=7.1 Hz, 2H), 2.42 (s, 3H), 1.33 (t, J=7.1 Hz, 3H), 1.14-0.93 (m, 6H).

$^{13}$C NMR (100 MHz, DMSO-d$_6$): δ 158.92, 144.08, 142.08, 133.58, 132.75, 131.61, 130.57, 129.88, 118.64, 112.39, 83.55, 60.78, 20.25, 16.34, 14.57.

Example 26 Preparation of ethyl 1-(allyloxy)-2-(3-cyanophenyl)-4-methyl-1H-imidazole-5-carboxylate (LY-26d)

The preparation in this example was basically the same as that of Example 24 except that the halogenated compound used herein was 3-bromopropene, and a white solid was obtained with a yield of 83.2% (Mp 94.7° C.-96.2° C.).

ESI-HRMS calcd. for $C_{17}H_{17}N_3O_3$ [M+H]$^+$ 312.1343, found: 312.1361.

$^1$H NMR (600 MHz, DMSO-d$_6$): δ 8.34-8.32 (m, 1H), 8.31-8.27 (m, 1H), 7.97 (dt, J=7.8, 1.4 Hz, 1H), 7.79-7.72 (m, 1H), 5.95-5.76 (m, 1H), 5.41-5.25 (m, 2H), 4.66 (d, J=6.4 Hz, 2H), 4.32 (q, J=7.1 Hz, 2H), 2.41 (s, 3H), 1.33 (t, J=7.1 Hz, 3H).

$^{13}$C NMR (100 MHz, DMSO-d$_6$): δ 158.83, 143.83, 140.95, 133.69, 132.35, 131.11, 130.71, 129.33, 123.02, 118.66, 112.56, 80.69, 60.85, 16.24, 14.56.

Example 27 Preparation of ethyl 2-(3-cyanophenyl)-1-(2-ethoxyethoxy)-4-methyl-1H-imidazole-5-carboxylate (LY-26e)

The preparation was basically the same as that of Example 24 except that the halogenated compound used herein was 2-bromoethyl ethyl ether, and a white solid was obtained with a yield of 84.6% (Mp 88.6° C.-89.4° C.).

ESI-HRMS calcd. for $C_{18}H_{21}N_3O_4$ [M+H]$^+$ 344.1605, found: 344.1619.

$^1$H NMR (600 MHz, DMSO-d$_6$): δ 8.46 (t, J=1.7 Hz, 1H), 8.39 (dt, J=8.1, 1.4 Hz, 1H), 7.95 (dt, J=7.7, 1.3 Hz, 1H), 7.70 (t, J=7.9 Hz, 1H), 4.37-4.25 (m, 4H), 3.59 (dd, J=4.9, 3.2 Hz, 2H), 3.35-3.33 (m, 2H), 2.40 (s, 3H), 1.32 (t, J=7.1 Hz, 3H), 1.09 (t, J=7.0 Hz, 3H).

$^{13}$C NMR (100 MHz, DMSO-d$_6$): δ 158.76, 143.93, 133.67, 132.57, 131.07, 130.45, 126.97, 118.76, 117.18, 112.48, 79.70, 67.18, 66.16, 60.84, 16.25, 15.30, 14.52.

Example 28 Preparation of ethyl 2-(3-cyanophenyl)-1-(3-hydroxypropoxy)-4-methyl-1H-imidazole-5-carboxylate (LY-26f)

The preparation was basically the same as that of Example 24 except that the halogenated compound used herein was 3-bromo-1-propanol, and a white solid was obtained with a yield of 75.2% (Mp 78.6° C.-80.4° C.).

ESI-HRMS calcd. for $C_{17}H_{19}N_3O_4$ [M+H]$^+$ 330.1448, found: 330.1483.

$^1$H NMR (600 MHz, DMSO-d$_6$): δ 8.33 (t, J=1.7 Hz, 1H), 8.30 (dt, J=8.1, 1.4 Hz, 1H), 7.96 (dt, J=7.7, 1.4 Hz, 1H), 7.74 (t, J=7.9 Hz, 1H), 4.54 (t, J=5.1 Hz, 1H), 4.31 (q, J=7.1 Hz, 2H), 4.15 (t, J=6.5 Hz, 2H), 3.48 (q, J=6.0 Hz, 2H), 2.40 (s, 3H), 1.80 (p, J=6.5 Hz, 2H), 1.33 (t, J=7.1 Hz, 3H).

$^{13}$C NMR (100 MHz, DMSO-d$_6$): δ 158.78, 143.93, 140.66, 133.71, 132.24, 131.09, 130.72, 129.10, 118.64, 117.08, 112.62, 78.14, 60.83, 57.62, 31.26, 16.22, 14.57.

Example 29 Preparation of ethyl 2-(3-cyanophenyl)-1-(2-ethoxy-2-oxoethoxy)-4-methyl-1H-imidazole-5-carboxylate (LY-26g)

The preparation was basically the same as that of Example 24 except that the halogenated compound used herein was ethyl bromoacetate, and a white solid was obtained with a yield of 79.8% (Mp 126.3° C.-127.7° C.).

ESI-HRMS calcd. for $C_{18}H_{19}N_3O_5$ [M+H]$^+$ 358.1397, found: 358.1431.

$^1$H NMR (600 MHz, DMSO-d$_6$): δ 8.41 (s, 1H), 8.33 (dt, J=8.1, 1.4 Hz, 1H), 7.96 (dt, J=7.8, 1.4 Hz, 1H), 7.73 (t, J=7.9 Hz, 1H), 4.95 (s, 2H), 4.31 (q, J=7.1 Hz, 2H), 4.13 (q, J=7.1 Hz, 2H), 2.41 (s, 3H), 1.31 (t, J=7.1 Hz, 3H), 1.18 (t, J=7.1 Hz, 3H).

$^{13}$C NMR (100 MHz, DMSO-d$_6$): δ 166.39, 158.74, 143.85, 140.75, 133.76, 132.54, 131.19, 130.58, 129.05, 118.72, 117.20, 112.51, 75.54, 61.60, 61.00, 16.26, 14.44, 14.32.

Example 30 Preparation of ethyl 1-(2-amino-2-oxoethoxy)-2-(3-cyanophenyl)-4-methyl-1H-imidazole-5-carboxylate (LY-26h)

The preparation was basically the same as that of Example 24 except that the halogenated compound used herein was 2-bromoacetamide, and a white solid was obtained with a yield of 86.7% (Mp 179.6° C.-181.2° C.).

ESI-HRMS calcd. for $C_{16}H_{16}N_4O_4$ [M+H]$^+$ 329.1244, found: 329.1364.

$^1$H NMR (600 MHz, DMSO-d$_6$): δ 8.51 (t, J=1.7 Hz, 1H), 8.38 (dt, J=8.1, 1.5 Hz, 1H), 7.95 (dt, J=7.8, 1.4 Hz, 1H), 7.72 (t, J=7.9 Hz, 1H), 7.66 (s, 1H), 7.54 (s, 1H), 4.62 (s, 2H), 4.31 (q, J=7.1 Hz, 2H), 2.41 (s, 3H), 1.32 (t, J=7.1 Hz, 3H).

$^{13}$C NMR (100 MHz, DMSO-d$_6$): δ 167.20, 158.79, 143.89, 140.67, 133.84, 132.48, 131.19, 130.59, 126.94, 118.71, 117.15, 112.63, 77.05, 61.00, 16.23, 14.47.

Example 31 Preparation of 3-{[2-(3-cyanophenyl)-5-(ethoxycarbonyl)-4-methyl-1H-imidazol-1-yl]oxy}propionic acid (LY-26i)

The preparation was basically the same as that of Example 24 except that the halogenated compound used herein was 3-bromopropionic acid, and a white solid was obtained with a yield of 75.4% (Mp 142.1° C.-143.9° C.).

MS (ESI) m/z: 344.2 [M+H]$^+$.

$^1$H NMR (400 MHz, DMSO-d$_6$): δ 12.52 (s, 1H), 8.46-8.27 (m, 2H), 7.95 (d, J=7.7 Hz, 1H), 7.71 (t, J=7.9 Hz, 1H), 4.42-4.18 (m, 4H), 2.67 (t, J=5.9 Hz, 2H), 2.41 (s, 3H), 1.33 (t, J=7.1 Hz, 3H).

$^{13}$C NMR (100 MHz, DMSO-d$_6$): δ 171.77, 158.80, 143.95, 140.78, 133.80, 132.41, 131.23, 130.59, 126.94, 118.67, 117.07, 112.68, 76.00, 60.87, 33.14, 16.26, 14.58.

Example 32 Preparation of ethyl 2-(3-cyanophenyl)-4-methyl-1-(pyridin-4-methoxy)-1H-imidazole-5-carboxylate (LY-26j)

The preparation was basically the same as that of Example 24 except that the halogenated compound used herein was 4-chloromethylpyridine, and a white solid was obtained with a yield of 76.2% (Mp 133.5° C.-135.1° C.).

ESI-HRMS calcd. for $C_{20}H_{18}N_4O_3$ [M+H]$^+$ 363.1452, found: 363.1471.

$^1$H NMR (600 MHz, DMSO-d$_6$): δ 8.58-8.42 (m, 2H), 8.14 (t, J=1.7 Hz, 1H), 8.11 (dt, J=8.1, 1.4 Hz, 1H), 7.92 (dt, J=7.8, 1.4 Hz, 1H), 7.66 (t, J=7.9 Hz, 1H), 7.31-7.23 (m, 2H), 5.19 (s, 2H), 4.34 (q, J=7.1 Hz, 2H), 2.44 (s, 3H), 1.31 (t, J=7.1 Hz, 3H).

$^{13}$C NMR (150 MHz, DMSO-d$_6$): δ 158.87, 150.26, 144.02, 141.67, 133.67, 132.49, 131.32, 130.55, 126.99, 124.24, 118.59, 116.95, 112.37, 79.87, 60.97, 16.36, 14.57.

Example 33 Preparation of ethyl 1-(benzyloxy)-2-(3-cyanophenyl)-4-methyl-1H-imidazole-5-carboxylate (LY-26k)

The preparation was basically the same as that of Example 24 except that the halogenated compound used herein was benzyl chloride, and a white solid was obtained with a yield of 79.1% (Mp 124.8° C.-126.3° C.).

ESI-HRMS calcd. for $C_{21}H_{20}N_3O_3$ [M+H]$^+$ 362.1499, found: 362.1539.

$^1$H NMR (600 MHz, DMSO-d$_6$): δ 8.13-8.09 (m, 2H), 7.90 (dt, J=7.7, 1.4 Hz, 1H), 7.65 (td, J=7.8, 0.6 Hz, 1H), 7.36-7.31 (m, 1H), 7.30-7.25 (m, 2H), 7.23-7.18 (m, 2H), 5.12 (s, 2H), 4.36 (q, J=7.1 Hz, 2H), 2.43 (s, 3H), 1.35 (t, J=7.1 Hz, 3H).

$^{13}$C NMR (100 MHz, DMSO-d$_6$): δ 158.93, 143.95, 141.46, 133.43, 132.95, 132.51, 131.21, 130.57, 130.35, 129.86, 129.17, 126.85, 118.62, 117.06, 112.25, 81.89, 60.90, 16.36, 14.63.

Example 34 Preparation of ethyl 2-(3-cyanophenyl)-1-[(2-fluorobenzyl)oxy]-4-methyl-1H-imidazole-5-carboxylate (LY-26l)

The preparation was basically the same as that of Example 24 except that the halogenated compound used herein was 2-fluorobenzyl bromide, and a white solid was obtained with a yield of 83.2% (Mp 135.5° C.-136.4° C.).

ESI-HRMS calcd. for $C_{21}H_{18}FN_3O_3[M+H]^+$ 380.1405, found: 380.1453.

$^1$H NMR (600 MHz, DMSO-d$_6$): δ 8.02 (s, 1H), 7.98 (d, J=8.0 Hz, 1H), 7.86 (d, J=7.7 Hz, 1H), 7.59 (t, J=7.8 Hz, 1H), 7.32 (d, J=6.9 Hz, 1H), 7.15 (t, J=7.1 Hz, 1H), 7.05 (t, J=7.4 Hz, 1H), 6.96 (t, J=9.2 Hz, 1H), 5.20 (s, 2H), 4.35 (q, J=7.0 Hz, 2H), 2.43 (s, 3H), 1.35 (t, J=7.0 Hz, 3H).

$^{13}$C NMR (100 MHz, DMSO-d$_6$): δ 158.92, 144.05, 141.86, 133.33, 132.73, 132.65, 132.58, 131.25, 130.16, 129.03, 124.81, 124.78, 118.61, 116.96, 115.69, 115.48, 112.10, 75.22, 60.90, 16.34, 14.59.

Example 35 Preparation of ethyl 2-(3-cyanophenyl)-1-[(3-fluorobenzyl)oxy]-4-methyl-1H-imidazole-5-carboxylate (LY-26m)

The preparation was basically the same as that of Example 24 except that the halogenated compound used herein was 3-fluorobenzyl bromide, and a white solid was obtained with a yield of 76.9% (Mp 136.3° C.-138.0° C.).

ESI-HRMS calcd. for $C_{21}H_{20}FN_3O_3[M+H]^+$ 380.1405, found: 380.1464.

$^1$H NMR (600 MHz, DMSO-d$_6$): δ 8.12-8.03 (m, 2H), 7.90 (dt, J=7.7, 1.4 Hz, 1H), 7.64 (t, J=7.8 Hz, 1H), 7.36-7.26 (m, 1H), 7.19-7.12 (m, 1H), 7.10-6.98 (m, 2H), 5.15 (s, 2H), 4.35 (q, J=7.1 Hz, 2H), 2.43 (s, 3H), 1.34 (t, J=7.1 Hz, 3H).

$^{13}$C NMR (100 MHz, DMSO-d$_6$): δ 158.93, 144.04, 141.75, 135.30, 133.50, 133.48, 132.60, 131.30, 130.67, 130.52, 130.28, 129.75, 129.08, 129.06, 118.59, 116.94, 112.22, 80.84, 60.93, 16.36, 14.60.

Example 36 Preparation of ethyl 2-(3-cyanophenyl)-1-[(4-fluorobenzyl)oxy]-4-methyl-1H-imidazole-5-carboxylate (LY-26n)

The preparation was basically the same as that of Example 24 except that the halogenated compound used herein was 4-fluorobenzyl bromide, and a white solid was obtained with a yield of 82.7% (Mp 140.7° C.-141.8° C.).

ESI-HRMS calcd. for $C_{21}H_{18}FN_3O_3[M+H]^+$ 380.1405, found: 380.1472.

$^1$H NMR (600 MHz, DMSO-d$_6$): δ 8.12-8.02 (m, 2H), 7.89 (d, J=7.7 Hz, 1H), 7.63 (t, J=7.8 Hz, 1H), 7.22 (dd, J=8.3, 5.5 Hz, 2H), 7.06 (t, J=8.6 Hz, 2H), 5.11 (s, 2H), 4.35 (q, J=7.1 Hz, 2H), 2.42 (s, 3H), 1.35 (t, J=7.1 Hz, 3H).

$^{13}$C NMR (100 MHz, DMSO-d$_6$): δ 158.93, 143.99, 141.64, 133.40, 133.06, 132.97, 132.51, 131.25, 130.26, 129.19, 118.60, 117.00, 115.80, 115.58, 112.18, 80.93, 60.90, 16.38, 14.62.

Example 37 Preparation of ethyl 1-[(2-chlorobenzyl)oxy]-2-(3-cyanophenyl)-4-methyl-1H-imidazole-5-carboxylate (LY-26o)

The preparation was basically the same as that of Example 24 except that the halogenated compound used herein was 2-chlorobenzyl chloride, and a white solid was obtained with a yield of 76.5% (Mp 124.6° C.-125.7° C.).

ESI-HRMS calcd. for $C_{21}H_{18}ClN_3O_3[M-H]^-$ 394.1037, found: 394.0975.

$^1$H NMR (400 MHz, DMSO-d$_6$): δ 7.96 (s, 1H), 7.90 (d, J=8.0 Hz, 1H), 7.82 (d, J=7.8 Hz, 1H), 7.54 (t, J=7.9 Hz, 1H), 7.27-7.21 (m, 1H), 7.22-7.15 (m, 3H), 5.24 (s, 2H), 4.35 (q, J=7.1 Hz, 2H), 2.43 (s, 3H), 1.35 (t, J=7.1 Hz, 3H).

$^{13}$C NMR (100 MHz, DMSO-d$_6$): δ 158.94, 144.16, 142.20, 134.86, 133.37, 133.22, 132.69, 131.89, 131.46, 130.81, 130.05, 129.62, 126.97, 127.55, 118.61, 116.86, 112.01, 78.84, 60.89, 16.38, 14.58.

Example 38 Preparation of ethyl 1-[(3-chlorobenzyl)oxy]-2-(3-cyanophenyl)-4-methyl-1H-imidazole-5-carboxylate (LY-26p)

The preparation was basically the same as that of Example 24 except that the halogenated compound used herein was 3-chlorobenzyl chloride, and a white solid was obtained with a yield of 83.8% (Mp 118.3° C.-119.7° C.).

ESI-HRMS calcd. for $C_{21}H_{18}ClN_3O_3[M+H]^+$ 396.1109, found: 396.1156.

$^1$H NMR (600 MHz, DMSO-d$_6$): δ 8.07-8.00 (m, 2H), 7.89 (dt, J=7.8, 1.4 Hz, 1H), 7.63 (t, J=7.8 Hz, 1H), 7.37-7.31 (m, 1H), 7.27 (t, J=7.8 Hz, 1H), 7.24 (t, J=1.8 Hz, 1H), 7.11 (dt, J=7.5, 1.3 Hz, 1H), 5.14 (s, 2H), 4.35 (q, J=7.1 Hz, 2H), 2.43 (s, 3H), 1.35 (t, J=7.1 Hz, 3H).

$^{13}$C NMR (100 MHz, DMSO-d$_6$): δ 158.91, 144.03, 141.69, 135.29, 133.48, 132.57, 131.27, 130.66, 130.50, 130.27, 129.74, 129.05, 116.92, 112.22, 80.82, 60.92, 16.36, 14.59.

Example 39 Preparation of ethyl 1-[(4-chlorobenzyl)oxy]-2-(3-cyanophenyl)-4-methyl-1H-imidazole-5-carboxylate (LY-26q)

The preparation was basically the same as that of Example 24 except that the halogenated compound used herein was 4-chlorobenzyl chloride, and a white solid was obtained with a yield of 76.2% (Mp 146.9° C.-148.3° C.).

ESI-HRMS calcd. for $C_{21}H_{18}ClN_3O_3[M+H]^+$ 396.1109, found: 396.1170.

$^1$H NMR (400 MHz, DMSO-d$_6$): δ 8.07-8.02 (m, 2H), 7.89 (dt, J=7.8, 1.4 Hz, 1H), 7.69-7.58 (m, 1H), 7.26 (d, J=8.4 Hz, 2H), 7.18 (d, J=8.4 Hz, 2H), 5.12 (s, 2H), 4.35 (q, J=7.1 Hz, 2H), 2.43 (s, 3H), 1.35 (t, J=7.1 Hz, 3H).

$^{13}$C NMR (100 MHz, DMSO-d$_6$): δ 158.91, 144.00, 134.82, 133.37, 132.49, 132.41, 131.93, 131.23, 130.24, 129.15, 126.81, 118.59, 112.18, 80.86, 60.90, 16.37, 14.61.

Example 40 Preparation of ethyl 1-[(4-bromobenzyl)oxy]-2-(3-cyanophenyl)-4-methyl-1H-imidazole-5-carboxylate (LY-26r)

The preparation was basically the same as that of Example 24 except that the halogenated compound used herein was 4-bromobenzyl chloride, and a white solid was obtained with a yield of 79.4% (Mp 137.6° C.-139.3° C.).

ESI-HRMS calcd. for $C_{21}H_{18}BrN_3O_3[M+H]^+$ 440.0604, found: 440.0653.

$^1$H NMR (600 MHz, DMSO-d$_6$): δ 8.08-8.00 (m, 2H), 7.90 (d, J=7.7 Hz, 1H), 7.63 (t, J=7.7 Hz, 1H), 7.42 (d, J=7.9 Hz, 2H), 7.11 (d, J=7.9 Hz, 2H), 5.12 (s, 2H), 4.35 (q, J=7.1 Hz, 2H), 2.43 (s, 3H), 1.35 (t, J=7.1 Hz, 3H).

$^{13}$C NMR (100 MHz, DMSO-d$_6$): δ 158.88, 143.99, 141.57, 133.34, 132.63, 132.44, 132.26, 131.75, 131.20, 130.22, 129.12, 123.54, 118.58, 112.19, 80.91, 60.90, 16.37, 14.60.

Example 41 Preparation of ethyl 2-(3-cyanophenyl)-4-methyl-1-[(4-methylbenzyl)oxy]-1H-imidazole-5-carboxylate (LY-26s)

The preparation was basically the same as that of Example 24 except that the halogenated compound used herein was 4-methylbenzyl chloride, and a white solid was obtained with a yield of 81.3% (Mp 119.4° C.-120.7° C.).

ESI-HRMS calcd. for $C_{22}H_{21}N_3O_3$ [M+H]$^+$ 376.1656, found: 376.1745.

$^1$H NMR (600 MHz, DMSO-d$_6$): δ 8.07-8.01 (m, 2H), 7.89 (dt, J=7.8, 1.3 Hz, 1H), 7.63 (t, J=7.8 Hz, 1H), 7.05-6.98 (m, 4H), 5.06 (s, 2H), 4.36 (q, J=7.1 Hz, 2H), 2.43 (s, 3H), 2.26 (s, 3H), 1.35 (t, J=7.1 Hz, 3H).

$^{13}$C NMR (100 MHz, DMSO-d$_6$): δ 158.93, 143.97, 141.66, 139.54, 133.27, 132.56, 131.16, 130.64, 130.14, 129.88, 129.33, 129.21, 118.64, 116.97, 112.08, 81.75, 60.86, 21.24, 16.36, 14.62.

Example 42 Preparation of ethyl 2-(3-cyanophenyl)-1-[(4-methoxybenzyl)oxy]-4-methyl-1H-imidazole-5-carboxylate (LY-26t)

The preparation was basically the same as that of Example 24 except that the halogenated compound used herein was 4-methoxybenzyl chloride, and a white solid was obtained with a yield of 74.2% (Mp 99.2° C.-101.3° C.).

ESI-HRMS calcd. for $C_{22}H_{21}N_3O_4$ [M+H]$^+$ 392.1605, found: 392.1635.

$^1$H NMR (400 MHz, DMSO-d$_6$): δ 8.17-7.99 (m, 2H), 7.87 (dt, J=7.8, 1.5 Hz, 1H), 7.71-7.52 (m, 1H), 7.07-6.97 (m, 2H), 6.80-6.68 (m, 2H), 5.04 (s, 2H), 4.36 (q, J=7.1 Hz, 2H), 3.72 (s, 3H), 2.42 (s, 3H), 1.36 (t, J=7.1 Hz, 3H).

$^{13}$C NMR (100 MHz, DMSO-d$_6$): δ 160.64, 158.96, 143.99, 141.78, 133.26, 132.53, 132.35, 131.21, 130.15, 129.27, 124.83, 118.65, 116.96, 114.11, 112.07, 81.62, 60.85, 55.59, 16.39, 14.64.

Example 43 Preparation of ethyl 2-(3-cyanophenyl)-1-{[4-(methoxycarbonyl)benzyl]oxy}-4-methyl-1H-imidazole-5-carboxylate (LY-26u)

The preparation was basically the same as that of Example 24 except that the halogenated compound used herein was 4-(methoxycarbonyl)benzyl chloride, and a white solid was obtained with a yield of 85.2% (Mp 167.5° C.-169.4° C.).

ESI-HRMS calcd. for $C_{23}H_{21}N_3O_5$ [M+H]$^+$ 420.1554, found: 420.1676.

$^1$H NMR (400 MHz, DMSO-d$_6$): δ 8.05 (dt, J=8.1, 1.4 Hz, 1H), 8.01 (t, J=1.6 Hz, 1H), 7.88 (dt, J=7.8, 1.3 Hz, 1H), 7.81 (d, J=8.3 Hz, 2H), 7.62 (t, J=7.9 Hz, 1H), 7.33 (d, J=8.2 Hz, 2H), 5.21 (s, 2H), 4.36 (q, J=7.1 Hz, 2H), 1.34 (t, J=7.1 Hz, 3H).

$^{13}$C NMR (100 MHz, DMSO-d$_6$): δ 166.14, 158.91, 144.04, 141.62, 137.99, 133.42, 132.58, 131.26, 130.79, 130.64, 130.32, 129.54, 129.09, 118.51, 116.96, 112.23, 80.98, 60.94, 52.71, 16.36, 14.60.

Example 44 Preparation of ethyl 2-(3-cyanophenyl)-4-methyl-1-[(4-nitrobenzyl)oxy]-1H-imidazole-5-carboxylate (LY-26v)

The preparation was basically the same as that of Example 24 except that the halogenated compound used herein was 4-nitrobenzyl chloride, and a white solid was obtained with a yield of 98.1% (Mp 159.8° C.-160.6° C.).

ESI-HRMS calcd. for $C_{21}H_{18}N_4O_5$ [M+H]$^+$ 407.1350, found: 407.1398.

$^1$H NMR (600 MHz, DMSO-d$_6$): δ 8.09 (d, J=8.6 Hz, 2H), 8.07-8.00 (m, 2H), 7.89 (dt, J=7.7, 1.4 Hz, 1H), 7.61 (t, J=7.8 Hz, 1H), 7.49 (d, J=8.6 Hz, 2H), 5.29 (s, 2H), 4.35 (q, J=7.1 Hz, 2H), 2.44 (s, 3H), 1.34 (t, J=7.1 Hz, 3H).

$^{13}$C NMR (100 MHz, DMSO-d$_6$): δ 158.90, 148.31, 144.05, 141.55, 140.35, 133.51, 132.55, 131.48, 131.36, 130.37, 129.05, 123.80, 116.93, 112.25, 80.26, 60.97, 16.37, 14.59.

Example 45 Preparation of ethyl 1-[(2-cyanobenzyl)oxy]-2-(3-cyanophenyl)-4-methyl-1H-imidazole-5-carboxylate (LY-26w)

The preparation was basically the same as that of Example 24 except that the halogenated compound used herein was 2-cyanobenzyl chloride, and a white solid was obtained with a yield of 73.9% (Mp 186.8° C.-188.4° C.).

ESI-HRMS calcd. for $C_{22}H_{18}N_4O_3$ [M+H]$^+$ 387.1452, found: 387.1481.

$^1$H NMR (400 MHz, DMSO-d$_6$): δ 7.91-7.79 (m, 3H), 7.62-7.52 (m, 2H), 7.56-7.46 (m, 1H), 7.42 (td, J=7.6, 1.3 Hz, 1H), 7.32 (d, J=8.0 Hz, 1H), 5.32 (s, 2H), 4.35 (q, J=7.1 Hz, 2H), 2.43 (s, 3H), 1.35 (t, J=7.1 Hz, 3H).

$^{13}$C NMR (100 MHz, DMSO-d$_6$): δ 158.94, 144.29, 142.20, 135.74, 133.45, 133.35, 133.21, 132.74, 132.50, 131.51, 130.77, 130.21, 128.94, 118.54, 116.98, 116.85, 113.50, 112.20, 79.22, 60.94, 16.38, 14.59.

Example 46 Preparation of ethyl 1-[(3-cyanobenzyl)oxy]-2-(3-cyanophenyl)-4-methyl-1H-imidazole-5-carboxylate (LY-26x)

The preparation was basically the same as that of Example 24 except that the halogenated compound used herein was 3-cyanobenzyl chloride, and a white solid was obtained with a yield of 76.8% (Mp 172.3° C.-173.7° C.).

ESI-HRMS calcd. for $C_{22}H_{18}N_4O_3$ [M+H]$^+$ 387.1452, found: 387.1466.

$^1$H NMR (400 MHz, DMSO-d$_6$): δ 8.11-7.96 (m, 2H), 7.89 (d, J=7.7 Hz, 1H), 7.75 (d, J=7.2 Hz, 1H), 7.67-7.57 (m, 2H), 7.52-7.38 (m, 2H), 5.21 (s, 2H), 4.36 (q, J=7.1 Hz, 2H), 2.43 (s, 3H), 1.35 (t, J=7.1 Hz, 3H).

$^{13}$C NMR (100 MHz, DMSO-d$_6$): δ 158.92, 144.08, 141.72, 135.23, 134.59, 134.26, 133.53, 133.40, 132.61, 131.35, 130.34, 130.05, 129.05, 118.55, 116.93, 112.22, 111.81, 80.40, 60.95, 16.38, 14.59.

Example 47 Preparation of ethyl 1-[(4-cyanobenzyl)oxy]-2-(3-cyanophenyl)-4-methyl-1H-imidazole-5-carboxylate (LY-26y)

The preparation was basically the same as that of Example 24 except that the halogenated compound used herein was 4-cyanobenzyl chloride, and a white solid was obtained with a yield of 81.6% (Mp 174.4° C.-176.3° C.).

ESI-HRMS calcd. for $C_{22}H_{18}N_4O_3$ [M+H]$^+$ 387.1452, found: 387.1540.

$^1$H NMR (400 MHz, DMSO-d$_6$): δ 8.10-7.98 (m, 2H), 7.90 (dt, J=7.8, 1.4 Hz, 1H), 7.72 (d, J=8.2 Hz, 2H), 7.63 (t, J=7.8 Hz, 1H), 7.41 (d, J=8.2 Hz, 2H), 5.23 (s, 2H), 4.35 (q, J=7.1 Hz, 2H), 2.44 (s, 3H), 1.33 (t, J=7.1 Hz, 3H).

$^{13}$C NMR (100 MHz, DMSO-d$_6$): δ 158.89, 144.02, 141.55, 138.34, 133.52, 132.69, 132.53, 131.33, 131.11, 130.37, 129.06, 118.76, 118.54, 116.95, 112.49, 112.26, 80.69, 60.95, 16.37, 14.59.

Example 48 Preparation of 4-methyl-2-(3-cyanophenyl)-1-methoxy-1H-imidazole-5-carboxylic acid (LY-27a)

The preparation was basically the same as that of Example 11 except that the starting material used herein was LY-26a, and a white solid was obtained with a yield of 91.2% (Mp 203.7° C.-205.3° C.).

ESI-HRMS calcd. for $C_{13}H_{11}N_3O_3$ [M−H]⁻ 256.0801, found: 256.0725.

$^1$H NMR (400 MHz, DMSO-d$_6$): δ 13.12 (s, 1H), 8.36-8.29 (m, 2H), 7.99-7.93 (m, 1H), 7.75 (t, J=7.8 Hz, 1H), 3.97 (s, 3H), 2.40 (s, 3H).

$^{13}$C NMR (100 MHz, DMSO-d$_6$): δ 160.19, 143.51, 140.01, 133.65, 132.12, 130.86, 130.81, 129.23, 118.75, 117.59, 112.67, 67.59, 16.21.

Example 49 Preparation of 4-methyl-2-(3-cyanophenyl)-1-ethoxy-1H-imidazole-5-carboxylic acid (LY-27b)

The preparation was basically the same as that of Example 11 except that the starting material used herein was LY-26b, and a white solid was obtained with a yield of 92.4%.

$^1$H NMR (400 MHz, DMSO-d$_6$): δ 13.13 (s, 1H), 8.34 (s, 1H), 8.32 (d, J=8.5 Hz, 1H), 7.96 (d, J=7.6 Hz, 1H), 7.76 (t, J=7.9 Hz, 1H), 4.17 (q, J=7.0 Hz, 2H), 2.40 (s, 3H), 1.21 (t, J=7.0 Hz, 3H).

$^{13}$C NMR (100 MHz, DMSO-d$_6$): δ 160.25, 143.44, 140.44, 133.57, 132.13, 131.01, 130.80, 129.45, 118.73, 117.87, 112.57, 76.20, 16.23, 13.47.

Example 50 Preparation of 4-methyl-2-(3-cyanophenyl)-1-allyloxy-1H-imidazole-5-carboxylic acid (LY-27d)

The preparation was basically the same as that of Example 11 except that the starting material used herein was LY-26d, and a white solid was obtained with a yield of 91.5% (Mp 176.6° C.-178.2° C.).

ESI-HRMS calcd. for $C_{15}H_{13}N_3O_3$ [M−H]⁻ 282.0957, found: 282.0882.

$^1$H NMR (400 MHz, DMSO-d$_6$): δ 13.15 (s, 1H), 8.33 (t, J=1.7 Hz, 1H), 8.30 (dt, J=7.9, 1.4 Hz, 1H), 7.95 (dt, J=7.8, 1.4 Hz, 1H), 7.74 (t, J=7.9 Hz, 1H), 5.83 (dt, J=16.9, 10.3, 6.5 Hz, 1H), 5.40-5.26 (m, 2H), 4.67 (d, J=6.5 Hz, 2H), 2.40 (s, 3H).

$^{13}$C NMR (100 MHz, DMSO-d$_6$): δ 160.30, 143.44, 140.76, 133.55, 132.35, 131.08, 130.88, 130.69, 129.55, 122.93, 118.72, 117.96, 112.52, 80.61, 16.25.

Example 51 Preparation of 4-methyl-2-(3-cyanophenyl)-1-benzyloxy-1H-imidazole-5-carboxylic acid (LY-27k)

The preparation was basically the same as that of Example 11 except that the starting material used herein was LY-26k, and a white solid was obtained with a yield of 90.2% (Mp 195.3° C.-197.4° C.).

ESI-HRMS calcd. for $C_{19}H_{15}N_3O_3$ [M−H]⁻ 332.1041, found: 332.1003.

$^1$H NMR (400 MHz, DMSO-d$_6$): δ 13.22 (s, 1H), 8.19-8.01 (m, 2H), 7.89 (dt, J=7.7, 1.4 Hz, 1H), 7.71-7.57 (m, 1H), 7.35-7.29 (m, 1H), 7.29-7.24 (m, 2H), 7.24-7.18 (m, 2H), 5.13 (s, 2H), 2.43 (s, 3H).

$^{13}$C NMR (100 MHz, DMSO-d$_6$): δ 160.43, 143.65, 141.15, 133.27, 133.06, 132.45, 131.13, 130.61, 130.32, 129.82, 129.37, 126.84, 118.67, 117.65, 112.21, 81.72, 16.31.

Example 52 Preparation of 4-methyl-2-(3-cyanophenyl)-1-(4-methylbenzyl)oxy-1H-imidazole-5-carboxylic acid (LY-27s)

The preparation was basically the same as that of Example 11 except that the starting material used herein was LY-26s, and a white solid was obtained with a yield of 81.2%.

$^1$HNMR (400 MHz, DMSO-d$_6$): δ 8.10-8.01 (m, 2H), 7.88 (dt, J=7.7, 1.4 Hz, 1H), 7.63 (t, J=7.9 Hz, 1H), 7.03 (d, 4H), 5.08 (s, 2H), 2.43 (s, 3H), 2.26 (s, 3H).

$^{13}$C NMR (100 MHz, DMSO-d$_6$): δ 167.82, 160.39, 143.68, 141.45, 139.51, 133.17, 132.56, 131.14, 130.67, 130.14, 130.00, 129.32, 118.69, 117.51, 112.04, 81.62, 21.25, 16.26.

Example 53 Preparation of 4-methyl-2-(3-cyanophenyl)-1-(4-cyanobenzyl)oxy-1H-imidazole-5-carboxylic acid (LY-27y)

The preparation was basically the same as that of Example 11 except that the starting material used herein was LY-26y, and a white solid was obtained with a yield of 92.4% (Mp 201.5° C.-202.3° C.).

ESI-HRMS calcd. for $C_{20}H_{14}N_4O_3$ [M−H]⁻ 357.1066, found: 357.0983.

$^1$H NMR (400 MHz, DMSO-d$_6$): δ 13.17 (s, 1H), 8.07-8.00 (m, 2H), 7.88 (dt, J=7.7, 1.4 Hz, 1H), 7.71 (d, J=8.1 Hz, 2H), 7.62 (t, J=7.8 Hz, 1H), 7.40 (d, J=8.2 Hz, 2H), 5.23 (s, 2H), 2.42 (s, 3H).

$^{13}$C NMR (100 MHz, DMSO-d$_6$): δ 160.35, 143.76, 141.22, 138.42, 133.34, 132.66, 132.44, 131.22, 131.10, 130.31, 129.23, 118.77, 118.57, 117.47, 112.46, 112.22, 80.56, 16.31.

Example 54 Preparation of 4-methyl-2-(3-cyanophenyl)-1-methoxy-N-propyl-1H-imidazole-5-carboxamide (LY-28a)

5 mmol of the compound LY-27a prepared in Example 48, 2.5 mmol of HBTU, mmol of triethylamine, 5 mmol of propylamine and 40 mL of N,N-dimethylformamide were mixed and then stirred for 8 h. The reaction mixture was poured into 80 mL of water and stirred for 10 min, and then filtered to collect a filter cake. The filter cake was washed twice with water and then dried to obtain a white solid with a yield of 80.6% (Mp 104.2° C.-105.8° C.).

ESI-HRMS calcd. for $C_{16}H_{18}N_4O_2$ [M+H]⁺ 299.1503, found: 299.1510.

Example 55 Preparation of 4-methyl-2-(3-cyanophenyl)-1-methoxy-N-isopropyl-1H-imidazole-5-carboxamide (LY-28b)

The preparation was basically the same as that of Example 54 except that the propylamine used in Example 54 was replaced with isopropyl amine, and a white solid was obtained with a yield of 82.9% (Mp 125.6° C.-126.5° C.).

ESI-HRMS calcd. for $C_{16}H_{18}N_4O_2$ [M+H]⁺ 299.1503, found: 299.1506.

$^1$H NMR (400 MHz, DMSO-d$_6$): δ 8.29 (dt, J=9.6, 1.3 Hz, 2H), 7.93 (d, J=7.8 Hz, 1H), 7.87 (d, J=7.9 Hz, 1H), 7.74 (t, J=7.7 Hz, 1H), 4.21-4.03 (m, 1H), 3.96 (s, 3H), 2.30 (s, 3H), 1.19 (d, J=6.6 Hz, 6H).

$^{13}$C NMR (100 MHz, DMSO-d$_6$): δ 157.87, 137.80, 137.30, 133.18, 131.56, 130.81, 130.30, 129.50, 121.84, 118.77, 112.67, 67.97, 41.16, 22.68, 14.95.

Example 56 Preparation of 4-methyl-2-(3-cyanophenyl)-1-methoxy-4-methyl-N-phenyl-1H-imidazole-5-form amide (LY-28c)

The preparation was basically the same as that of Example 54 except that the propylamine used in Example 54 was replaced with aniline, and a white solid was obtained with a yield of 84.2% (Mp 143.8° C.-145.2° C.).

ESI-HRMS calcd. for $C_{19}H_{16}N_4O_2$ [M+H]$^+$ 333.1346, found: 333.1364.

$^1$H NMR (400 MHz, DMSO-d$_6$): δ 10.13 (s, 1H), 8.37-8.32 (m, 2H), 7.97 (dt, J=7.8, 1.4 Hz, 1H), 7.77 (td, J=7.7, 0.9 Hz, 1H), 7.74-7.69 (m, 2H), 7.37 (t, 2H), 7.18-7.09 (m, 1H), 4.01 (s, 3H), 2.37 (s, 3H).

$^{13}$C NMR (100 MHz, DMSO-d$_6$): δ 157.33, 139.00, 138.48, 138.10, 133.44, 131.70, 130.92, 130.44, 129.34, 129.26, 124.47, 122.12, 120.49, 118.77, 112.76, 68.27, 15.06.

Example 57 Preparation of ethyl 2-(3-cyanophenyl)-4-methyl-1H-imidazole-5-carboxylate (LY-29)

2.6 g (10 mmol) of the compound LY-10 prepared in Example 10 was added into a 100 mL flask, to which 10 mmol of potassium iodide, 15 mmol of trimethylchlorosilane and 30 mL of N,N-dimethylformamide were added. The reaction mixture was heated to 60° C. and then reacted for 6 h. After the reaction was completed, the reaction mixture was poured into a 1 mol/L aqueous sodium hydroxide solution and stirred for 1 h to precipitate a white crude product. The crude product was recrystallized with a mixture of N,N-dimethylformamide and water in a volume ratio of 1:1 to obtain a white solid with a yield of 77.3% (Mp 209.6° C.-210.7° C.).

ESI-HRMS calcd. for $C_{15}H_{15}N_3O_2$ [M–H]– 254.0935, found: 254.0959.

$^1$H NMR (400 MHz, DMSO-d$_6$): δ 8.35 (s, 1H), 8.28 (d, J=8.0 Hz, 1H), 7.80 (d, J=7.7 Hz, 1H), 7.65 (t, J=7.8 Hz, 1H), 4.80 (s, 1H), 4.25 (q, J=7.1 Hz, 2H), 2.47 (s, 3H), 1.30 (t, J=7.1 Hz, 3H).

$^{13}$C NMR (100 MHz, DMSO-d$_6$): δ 162.99, 144.34, 140.85, 132.04, 130.50, 130.13, 128.92, 126.99, 118.97, 112.31, 59.83, 14.86, 12.89.

Example 58 Preparation of ethyl 1,4-dimethyl-2-(3-cyanophenyl)-1H-imidazole-5-carboxylate (LY-30)

The preparation was basically the same as that of Example 23 except that the starting material used herein was LY-29, and a white solid was obtained with a yield of 76.2% (Mp 137.3° C.-138.1° C.).

ESI-HRMS calcd. for $C_{15}H_{15}N_3O_2$ [M+H]$^+$ 270.1237, found: 270.1250.

$^1$H NMR (400 MHz, DMSO-d$_6$): δ 8.13 (s, 1H), 8.07-7.91 (m, 2H), 7.73 (t, J=7.8 Hz, 1H), 4.30 (q, J=7.3 Hz, 2H), 3.84 (s, 3H), 2.42 (s, 3H), 1.33 (t, J=7.1 Hz, 3H).

$^{13}$C NMR (100 MHz, DMSO-d$_6$): δ 160.95, 148.48, 146.87, 134.35, 133.45, 132.92, 131.23, 130.38, 120.94, 118.74, 112.32, 60.54, 35.03, 16.05, 14.65.

Example 59 Preparation of ethyl 2-(3-cyano-4-fluorophenyl)-1-hydroxy-4-methyl-1H-imidazole-5-carboxylate (LY-F1)

The preparation was basically the same as that of Example 6 except that the halogenated compound used herein was 4-fluoro-3-cyanobenzaldehyde, and a white solid was obtained with a yield of 80.2%.

$^1$H NMR (400 MHz, DMSO-d$_6$): δ 12.32 (s, 1H), 8.52-8.26 (m, 1H), 7.74-7.56 (m, 1H), 4.29 (q, J=7.1 Hz, 1H), 2.37 (s, 1H), 1.32 (t, J=7.1 Hz, 3H).

Example 60 Preparation of tablets of ethyl 1-[(4-cyanobenzyl)oxy]-2-(3-cyanophenyl)-4-methyl-1H-imidazole-5-carboxylate (LY-26y)

A pharmaceutical composition consisting of 50 g of LY-26y, 114 g of lactose, 142 g of microcrystalline cellulose, 24 g of sodium carboxymethyl starch and 5 g of magnesium stearate was prepared into tablets herein in a total number of 1000.

A coating liquid containing 21 g of Opadry (03B26796) and an appropriate amount of 95% ethanol was prepared herein to a volume of about 430 mL.

Specifically, the auxiliary materials that had passed through a 100 mesh sieve in advance and the main drug that had passed through a 60 mesh sieve in advance were mixed uniformly and then added with 95% ethanol to produce a soft material. The soft material was granulated by an 18 mesh sieve, dried at 60° C. under ventilation and pelletized with a 16 mesh sieve. Then the pelletized product was mixed with magnesium stearate after sieving and punched to tablets by a Φ6 mm shallow indentation.

The coating liquid was prepared as follows. An appropriate amount of 95% ethanol was added to a container, to which the prescribed dose of Opadry (03B26796) powder was evenly added under stirring. During the addition process of the Opadry (03B26796) powder, the stirring rate can be increased to avoid the powder floating on the liquid surface. After the Opadry was completely added, the stirring was reduced to a speed under which the vortex disappeared, and continuously performed for 45 min to produce the coating liquid.

The film-coated tablets were prepared as follows. The tablet core was put into a pot and kept at 60° C.±5° C. for coating to obtain the film-coated tablets.

Example 61 Preparation of capsule of ethyl 1-[(4-cyanobenzyl)oxy]-2-(3-cyanophenyl)-4-methyl-1H-imidazole-5-carboxylate (LY-26y)

A pharmaceutical composition consisting of 50 g of LY-26y, 250 g of PEG-400, 250 g of 1,2-propanediol and 125 g of tween-80 was prepared into capsules herein in a total number of 1000.

Specifically, a prescribed dose of ethyl 1-[(4-cyanobenzyl)oxy]-2-(3-cyanophenyl)-4-methyl-1H-imidazole-5-carboxylate was mixed with PEG-400, 1,2-propanediol and tween-80 at 40° C. for complete dissolution. Then the mixture was cooled to room temperature and processed into capsules.

Example 62 Investigation on Inhibition of ADP-Induced Platelet Aggregation in Rabbit 1. Plasma Preparation A blood sample was collected from ear vein of a healthy male rabbit, added with 3.8% sodium citrate for anticoagulation and then centrifuged at 800 r/min for 10 min to prepare platelet-rich plasma (PRP) and at 3,000 r/min for 10 min to prepare platelet-poor plasma (PPP). The investigation on the plasma should be performed within 0.5-3 h after the preparation.

2. Determination of Platelet Aggregation by Microplate Method

The drugs to be tested were weighed and added with an appropriate amount of DMSO to prepare a series of 10 mM stock solutions, which were respectively diluted to prepare 10× stock solutions with normal saline for further use.

Several wells of a microplate were selected as test wells, which were added with 135 μL of PRP and then respectively added with 15 μL of the 10× stock solutions. A well in which 135 μL of PRP and 15 μL of normal saline were added was used as the vehicle control, and a well in which 135 μL of PPP and 15 μL of normal saline were added was used as the blank control. Duplicate wells were set for each test well. The plate was shaken, incubated at 37° C. for 5 min, and then measured for $A_0$ at 655 nm. Subsequently, the microplate was added with 15 μL of an inducer diphosphate (ADP) working solution (25 μmol/L) in each well, incubated at 37° C. under shaking and measured at 655 nm for A1, where the incubation time was determined according to the time in the pre-experiment when the maximum aggregation appeared. The platelet aggregation rate (AR) and platelet aggregation inhibition rate (AIR) were calculated according to the following formulas:

$$AR=(A_0-A1)/(A_0-A_{ppp})$$

$$AR=(1-AR_{test\ sample}/AR_{control})$$

$IC_{50}$ values of individual target compounds were shown in Table 1.

TABLE 1

$IC_{50}$ values of target compounds (Mean±SE)

| Compound | $IC_{50}$ (μM) |
|---|---|
| LY-7a | 16.825 ± 0.874 |
| LY-7b | 19.045 ± 0.317 |
| LY-7c | 8.852 ± 0.427 |
| LY-8a | 5.214 ± 0.0152 |
| LY-8b | 18.330 ± 1.026 |
| LY-10 | 17.636 ± 0.952 |
| LY-11 | 7.865 ± 0.0365 |
| LY-13 | 21.856 ± 0.865 |
| LY-15 | 22.069 ± 0.299 |
| LY-16 | 19.865 ± 0.126 |
| LY-19 | 14.857 ± 0.0568 |
| LY-22 | 13.353 ± 1.035 |
| LY-25 | 24.12%[a] |
| LY-26a | 9.134 ± 0.346 |
| LY-26b | 16.529 ± 1.068 |
| LY-26c | 6.736 ± 0.326 |
| LY-26d | 5.856 ± 0.0165 |
| LY-26e | 6.247 ± 0.210 |
| LY-26f | 11.352 + 0.213 |
| LY-26g | 6.796 ± 0.152 |
| LY-26h | 18.87%[a] |
| LY-26i | 24.35%[a] |
| LY-26j | 6.196 ± 0.0526 |
| LY-26k | 5.934 ± 0.265 |
| LY-26l | 5.879 ± 0.196 |
| LY-26m | 22.358 ± 1.358 |
| LY-26n | 5.879 ± 0.196 |
| LY-26o | 8.705 ± 0.242 |
| LY-26p | 19.357 ± 0.355 |
| LY-26q | 6.825 ± 0.265 |
| LY-26r | 24.590 ± 0.895 |
| LY-26s | 6.311 ± 0.399 |
| LY-26t | 6.826 ± 0.0856 |
| LY-26u | 9.466 ± 0.856 |
| LY-26v | 8.754 ± 0.159 |
| LY-26w | 9.376 ± 0.565 |
| LY-26x | 3.21%[a] |
| LY-26y | 4.237 ± 0.0156 |
| LY-27a | 7.987 ± 0.217 |

TABLE 1-continued $IC_{50}$ values of target compounds (Mean±SE)

| Compound | $IC_{50}$ (μM) |
|---|---|
| LY-27b | 9.715 ± 0.557 |
| LY-27d | 6.350 ± 0.469 |
| LY-27k | 6.238 ± 0.324 |
| LY-27s | 6.563 ± 0.357 |
| LY-27y | 3.875 ± 0.269 |
| LY-28a | 9.569 ± 0.226 |
| LY-28b | 11.240 ± 0.966 |
| LY-28c | 15.892 ± 1.203 |
| LY-29 | 32.52%[a] |
| LY-30a | 22.136 ± 0.703 |
| LY-30b | 19.854 ± 0.956 |
| LY-30c | 9.259 ± 0.499 |
| Ticagrelor | 7.213 ± 0.251 |

[a]Inhibition rate of target compounds on platelet aggregation at 30 μM

Example 63 Effect of Intragastric Administration of Compound LY-26y on Arterial Thrombosis in Male Sprague Dawley (SD) Rats 1. Experimental animals: 50 male SD rats, 260-320 g (n=10).

2. Main reagents: ferric chloride, urethane, 0.5% CMC-Na, 0.9% NaCl.

The 50 male SD rats were randomly and averagely divided into five groups, respectively model group, low-dose LY-26y group (5 mg/kg), medium-dose LY-26y group (10 mg/kg), high-dose LY-26y group (20 mg/kg) and positive control group (10 mg/kg ticagrelor). After experiencing one-week adaptation, the rats in the experimental groups were treated by intragastric administration of LY-26y by at 9 am every day, and the model group was treated with 0.5% CMC-Na solution. After continuously treated for one week, the rats were anesthetized by intraperitoneal injection of 20% urethane (0.6 mL/10 g) 8 min after the last administration. Then the anesthetized rats were placed on an insulation plate (to maintain body temperature) in a supine position, and a straight incision was made on the midline of the neck to expose the right common carotid artery. A plastic film (1.5×1.0 cm²) was placed under the artery to protect the surrounding tissues. The filter paper was cut into a size of 1.0×0.8 cm², soaked with a 20% $FeCl_3$ solution and then used to coat the exposed artery for 30 min to induce venous thrombosis. After 2 h of the administration, a 1.5-cm left carotid artery was collected and weighed, and then the blood vessel was cut to remove the thrombus therein to measure the weight of the blood vessel wall, where the weight difference was the weight of thrombus. The weight of carotid artery thrombus induced by ferric chloride was shown in Table 2.

TABLE 2

Weight of carotid artery thrombus induced by ferric chloride

| Drugs | Dose (mg/kg) | Wet weight of thrombus (mg) |
|---|---|---|
| Model group | — | 8.24 ± 0.39 |
| LY-26y | 5 | 6.38 ± 0.18 |
|  | 10 | 4.89 ± 0.33 |
|  | 20 | 4.39 ± 0.26 |
| Ticagrelor | 10 | 5.01 ± 0.16 |

The intragastric administration of compound LY-26y significantly reduced the weight of the $FeCl_3$-induced arterial thrombus in rats (as shown in the FIGURE).

The above results demonstrated that the compounds provided herein had significant activity in inhibiting the formation of thrombus, and thus were promising for the preparation of related medicines and/or pharmaceutical compositions.

The above-mentioned embodiments are only illustrative of the technical concept and features of the disclosure, and are merely intended to enable those skilled in the art to understand and implement the disclosure. It should be noted that the disclosure is not limited to these embodiments. Any changes or modifications made without departing from the spirit of the disclosure should fall within the scope of the disclosure.

What is claimed is:

1. A compound, or a pharmaceutically-acceptable salt, a tautomer or a pharmaceutically-acceptable solvate thereof, the compound being selected from the group consisting of:
    ethyl 1-acetoxy-2-(3-cyano-4-isobutoxyphenyl)-4-methyl-1H-imidazole-5-carboxylate;
    ethyl 2-(3-cyano-4-hydroxyphenyl)-1-hydroxy-4-methyl-1H-imidazole-5-carboxylate;
    ethyl 2-(3-cyanophenyl)-1-hydroxy-4-methyl-1H-imidazole-5-carboxylate;
    ethyl 2-[3-(1H-tetrazol-5-yl)phenyl]-1-hydroxy-4-methyl-1H-imidazole-5-carboxylate;
    ethyl 1-hydroxy-4-methyl-2-[3-(5-oxo-4,5-dihydro-1,2,4-oxadiazol-3-yl)phenyl]-1H-imidazole-5-carboxylate;
    ethyl 2-(3-cyanophenyl)-1-hydroxy-4-phenyl-1H-imidazole-5-carboxylate;
    ethyl 2-(2-cyanophenyl)-1-hydroxy-4-methyl-1H-imidazole-5-carboxylate;
    ethyl 2-(4-cyanophenyl)-1-methoxy-4-methyl-1H-imidazole-5-carboxylate;
    ethyl 1-methoxy-2,4-dimethyl-2-phenyl-1H-imidazole-5-carboxylate;
    ethyl 2-(3-cyanophenyl)-1-methoxy-4-methyl-1H-imidazole-5-carboxylate;
    ethyl 2-(3-cyanophenyl)-1-ethoxy-4-methyl-1H-imidazole-5-carboxylate;
    ethyl 2-(3-cyanophenyl)-1-isopropoxy-4-methyl-1H-imidazole-5-carboxylate;
    ethyl 1-(allyloxy)-2-(3-cyanophenyl)-4-methyl-1H-imidazole-5-carboxylate;
    ethyl 2-(3-cyanophenyl)-1-(2-ethoxyethoxy)-4-methyl-1H-imidazole-5-carboxylate;
    ethyl 2-(3-cyanophenyl)-1-(3-hydroxypropoxy)-4-methyl-1H-imidazole-5-carboxylate;
    ethyl 2-(3-cyanophenyl)-1-(2-ethoxy-2-oxoethoxy)-4-methyl-1H-imidazole-5-carboxylate;
    ethyl 1-(2-amino-2-oxoethoxy)-2-(3-cyanophenyl)-4-methyl-1H-imidazole-5-carboxylate;
    2-{[2-(3-cyanophenyl)-5-(ethoxycarbonyl)-4-methyl-1H-imidazol-1-yl]oxy}acetic acid;
    ethyl 2-(3-cyanophenyl)-4-methyl-1-(pyridin-4-methoxy)-1H-imidazole-5-carboxylate;
    ethyl 1-(benzyloxy)-2-(3-cyanophenyl)-4-methyl-1H-imidazole-5-carboxylate;
    ethyl 2-(3-cyanophenyl)-1-[(2-fluorobenzyl)oxy]-4-methyl-1H-imidazole-5-carboxylate;
    ethyl 2-(3-cyanophenyl)-1-[(3-fluorobenzyl)oxy]-4-methyl-1H-imidazole-5-carboxylate;
    ethyl 2-(3-cyanophenyl)-1-[(4-fluorobenzyl)oxy]-4-methyl-1H-imidazole-5-carboxylate;
    ethyl 1-[(2-chlorobenzyl)oxy]-2-(3-cyanophenyl)-4-methyl-1H-imidazole-5-carboxylate;
    ethyl 1-[(3-chlorobenzyl)oxy]-2-(3-cyanophenyl)-4-methyl-1H-imidazole-5-carboxylate;
    ethyl 1-[(4-chlorobenzyl)oxy]-2-(3-cyanophenyl)-4-methyl-1H-imidazole-5-carboxylate;
    ethyl 1-[(4-bromobenzyl)oxy]-2-(3-cyanophenyl)-4-methyl-1H-imidazole-5-carboxylate;
    ethyl 2-(3-cyanophenyl)-4-methyl-1-[(4-methylbenzyl)oxy]-1H-imidazole-5-carboxylate;
    ethyl 2-(3-cyanophenyl)-1-[(4-methoxybenzyl)oxy]-4-methyl-1H-imidazole-5-carboxylate;
    ethyl 2-(3-cyanophenyl)-1-{[4-(methoxycarbonyl)benzyl]oxy}-4-methyl-1H-imidazole-5-carboxylate;
    ethyl 2-(3-cyanophenyl)-4-methyl-1-[(4-nitrobenzyl)oxy]-1H-imidazole-5-carboxylate;
    ethyl 1-[(2-cyanobenzyl)oxy]-2-(3-cyanophenyl)-4-methyl-1H-imidazole-5-carboxylate;
    ethyl 1-[(3-cyanobenzyl)oxy]-2-(3-cyanophenyl)-4-methyl-1H-imidazole-5-carboxylate;
    ethyl 1-[(4-cyanobenzyl)oxy]-2-(3-cyanophenyl)-4-methyl-1H-imidazole-5-carboxylate;
    2-(3-cyanophenyl)-1-hydroxy-4-methyl-1H-imidazole-5-carboxylic acid;
    2-(3-cyanophenyl)-1-methoxy-4-methyl-1H-imidazole-5-carboxylic acid;
    2-(3-cyanophenyl)-1-ethoxy-4-methyl-1H-imidazole-5-carboxylic acid;
    1-(allyloxy)-2-(3-cyanophenyl)-4-methyl-1H-imidazole-5-carboxylic acid;
    1-(benzyloxy)-2-(3-cyanophenyl)-4-methyl-1H-imidazole-5-carboxylic acid;
    2-(3-cyanophenyl)-4-methyl-1-[(4-methylbenzyl)oxy]-1H-imidazole-5-carboxylic acid;
    1-[(4-cyanobenzyl)oxy]-2-(3-cyanophenyl)-4-methyl-1H-imidazole-5-carboxylic acid;
    2-(3-cyanophenyl)-1-methoxy-4-methyl-N-propyl-1H-imidazole-5-carboxamide;
    2-(3-cyanophenyl)-N-isopropyl-1-methoxy-4-methyl-1H-imidazole-5-carboxamide;
    2-(3-cyanophenyl)-1-methoxy-4-methyl-N-phenyl-1H-imidazole-5-carboxamide;
    ethyl 2-(3-cyanophenyl)-1,4-dimethyl-1H-imidazole-5-carboxylate; and
    ethyl 2-(3-cyano-4-fluorophenyl)-1-hydroxy-4-methyl-1H-imidazole-5-carboxylate.

2. A pharmaceutical composition, comprising:

the compound of claim 1, or a pharmaceutically-acceptable salt, a tautomer or a pharmaceutically-acceptable solvate thereof; and a pharmaceutically-acceptable carrier.

3. A method for preparing the compound of formula (I), or a pharmaceutically-acceptable salt thereof, comprising:

subjecting a substituted benzaldehyde and ethyl 2-hydroxyimino-3-oxobutyrate to cyclization reaction to obtain an intermediate ethyl 2-aryl-1-hydroxy-4-methyl-1H-imidazole-5-carboxylate; and subjecting the intermediate to alkylation with a halogenated hydrocarbon followed by hydrolysis or ammonolysis to produce the compound of formula (I)

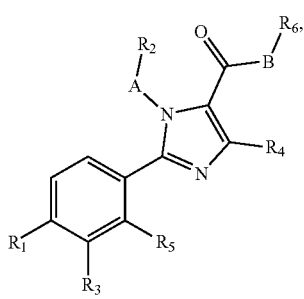

(I)

wherein $R_1$ is selected from the group consisting of hydrogen, hydroxyl, cyano, tetrazolyl, triazolyl, imidazolyl, nitro, halogen, $C_1$-$C_8$ linear and branched alkyl, $C_3$-$C_8$ cycloalkyl, $C_1$-$C_8$ linear and branched alkyloxy, $C_3$-$C_8$ cycloalkyloxy, $C_1$-$C_8$ linear and branched aliphatic alkylamino, $C_3$-$C_8$ aliphatic cycloalkylamino, $C_2$-$C_8$ linear and branched alkenyl, $C_2$-$C_8$ linear and branched alkenyloxy, $C_2$-$C_8$ linear and branched alkenylamino, $C_2$-$C_8$ linear and branched alkynyl, $C_2$-$C_8$ linear and branched alkynyloxy, $C_2$-$C_8$ linear and branched alkynylamino, and substituted and unsubstituted $C_6$-$C_{10}$ aryl, wherein a substituent on the substituted $C_6$-$C_{10}$ aryl is selected from the group consisting of halogen, hydroxyl, cyano, nitro, $C_1$-$C_6$ alkyl, $C_1$-$C_6$ alkyloxy, $C_1$-$C_6$ alkylamino, $C_1$-$C_6$ alkylcarbonyl, $C_1$-$C_6$ alkyloxycarbonyl and $C_1$-$C_6$ alkylaminocarbonyl;

$R_2$ is selected from the group consisting of hydrogen, hydroxyl, $C_1$-$C_8$ linear and branched alkyl, $C_3$-$C_8$ cycloalkyl, $C_2$-$C_8$ linear and branched alkenyl, $C_2$-$C_8$ linear and branched alkynyl, —$(CH_2)_n$—COOH, —$(CH_2)_n$—OH, —$(CH_2)_n$—CONH$_2$, —$(CH_2)_n$—NHOC$(CH_2)_m$CH$_3$, —$(CH_2)_n$—COOC$(CH_2)_m$CH$_3$, and substituted and unsubstituted $C_6$-$C_{10}$ aryl, wherein a substituent on the substituted $C_6$-$C_{10}$ aryl is selected from the group consisting of halogen, hydroxyl, cyano, nitro, $C_1$-$C_6$ alkyl, $C_1$-$C_6$ alkyloxy, $C_1$-$C_6$ alkylamino, —$(CH_2)_n$—COOH, —$(CH_2)_n$—OH, —$(CH_2)_n$—CONH$_2$, —$(CH_2)_n$—NHOC$(CH_2)_m$CH$_3$ and —$(CH_2)_n$—COOC$(CH_2)_m$CH$_3$; and n is selected from 1-6, and m is selected from 1-3;

A is selected from the group consisting of nitrogen atom, oxygen atom, hydrogen atom, carbon atom, and sulfur atom;

$R_3$ is selected from the group consisting of hydrogen, cyano, tetrazolyl, triazolyl, imidazolyl, 1,2,4-oxadiazolyl, nitro, halogen, $C_1$-$C_6$ alkyl, $C_1$-$C_6$ alkylamino, and $C_1$-$C_6$ alkoxy;

$R_4$ is selected from the group consisting of $C_1$-$C_6$ alkyl and substituted and unsubstituted $C_6$-$C_{10}$ aryl, wherein a substituent on the substituted aryl is selected from the group consisting of halogen, $C_1$-$C_6$ alkylamino, $C_1$-$C_6$ alkyl, $C_1$-$C_6$ alkoxy, nitro, hydroxyl, cyano, and amino;

$R_5$ is selected from the group consisting of hydrogen, cyano, tetrazolyl, triazolyl, imidazolyl, 1,2,4-oxadiazolyl, nitro, fluorine, chlorine, bromine, $C_1$-$C_6$ alkyl, $C_1$-$C_6$ alkylamino, and $C_1$-$C_6$ alkoxy;

$R_6$ is selected from the group consisting of hydrogen, $C_1$-$C_6$ alkyl, $C_1$-$C_6$ alkylamino, $C_1$-$C_6$ alkoxy and substituted and unsubstituted $C_6$-$C_{10}$ aryl, wherein a substituent on the substituted aryl is selected from the group consisting of halogen, $C_1$-$C_6$ alkylamino, $C_1$-$C_6$ alkoxy, $C_1$-$C_6$ alkyl, nitro, hydroxyl, cyano, and amino; and B is selected from the group consisting of oxygen atom, nitrogen atom, carbon atom, sulfur atom, and NH.

4. A platelet aggregation inhibitor, comprising:
the compound of claim 1, or a pharmaceutically-acceptable salt, a tautomer or a pharmaceutically-acceptable solvate thereof.

5. A drug for treating thrombosis, comprising:
the compound of claim 1, or a pharmaceutically-acceptable salt, a tautomer or a pharmaceutically-acceptable solvate thereof.

* * * * *